United States Patent
Morris et al.

(10) Patent No.: US 6,790,220 B2
(45) Date of Patent: Sep. 14, 2004

(54) METHOD AND APPARATUS FOR SEALING ACCESS

(75) Inventors: Edward J. Morris, Bloomington, IN (US); Andrew J. DeNardo, Carmel, IN (US)

(73) Assignee: Morris Innovative Research, Inc., Bloomington, IN (US)

( * ) Notice: Subject to any disclaimer, the term of this patent is extended or adjusted under 35 U.S.C. 154(b) by 0 days.

(21) Appl. No.: 10/166,399

(22) Filed: Jun. 10, 2002

(65) Prior Publication Data

US 2002/0188319 A1 Dec. 12, 2002

Related U.S. Application Data

(60) Provisional application No. 60/297,060, filed on Jun. 8, 2001.

(51) Int. Cl.⁷ .............................................. A61B 17/08
(52) U.S. Cl. ..................................... 606/213; 606/151
(58) Field of Search .............................. 606/213, 214, 606/232, 151; 623/1.13, 1.11

(56) References Cited

U.S. PATENT DOCUMENTS

| | | | |
|---|---|---|---|
| 3,562,820 A | * 2/1971 | Braun | 623/23.64 |
| 4,852,568 A | * 8/1989 | Kensey | 606/213 |
| 4,902,508 A | * 2/1990 | Badylak et al. | 424/423 |
| 5,151,105 A | * 9/1992 | Kwan-Gett | 623/1.32 |
| 5,531,759 A | * 7/1996 | Kensey et al. | 606/213 |
| 5,549,633 A | 8/1996 | Evans et al. | |
| 5,649,959 A | * 7/1997 | Hannam et al. | 606/213 |
| 5,733,337 A | 3/1998 | Carr et al. | |
| 5,928,266 A | 7/1999 | Kontos | |
| 6,110,459 A | * 8/2000 | Mickle et al. | 424/93.21 |
| 6,358,284 B1 | * 3/2002 | Fearnot et al. | 623/23.72 |

* cited by examiner

*Primary Examiner*—Michael J. Milano
*Assistant Examiner*—Jessica R Baxter
(74) *Attorney, Agent, or Firm*—Barnes & Thornburg

(57) ABSTRACT

The present invention relates to an apparatus and a method for sealing a puncture in a tubular tissue structure or the wall of a body cavity. More specifically, the present invention is directed to an apparatus and method for sealing a puncture site in the wall of a tubular tissue structure, or in the wall of a body cavity with submucosal tissue or another extracellular or matrix-derived tissue capable of remodeling endogenous connective tissue in vivo. The submucosal tissue or another extracellular matrix-derived tissue is inserted into the puncture site as a sheet on an introducer element such as a needle, a cannula, a guide wire, an introducer element adapted for dialysis, an introducer element adapted for catheterization, a trocar, or any other introducer element used to access the lumen of a tubular tissue structure or used to access a body cavity.

10 Claims, 48 Drawing Sheets

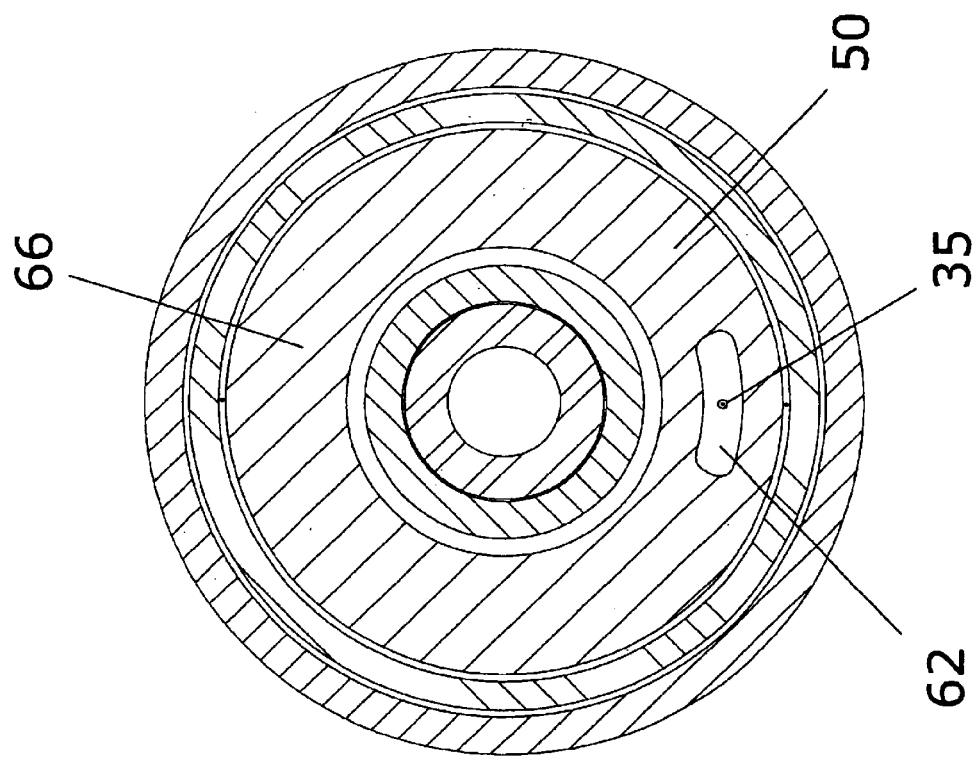

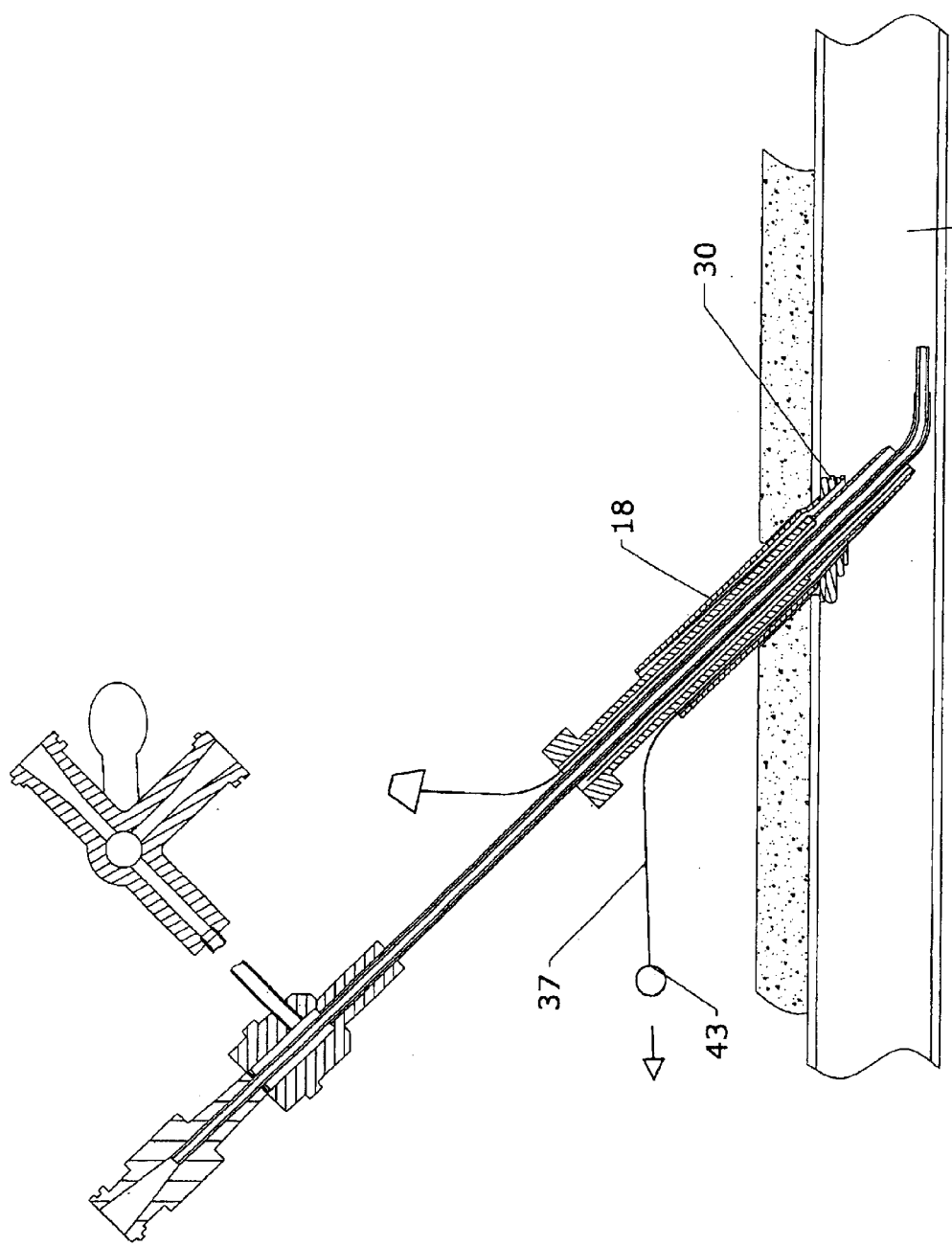

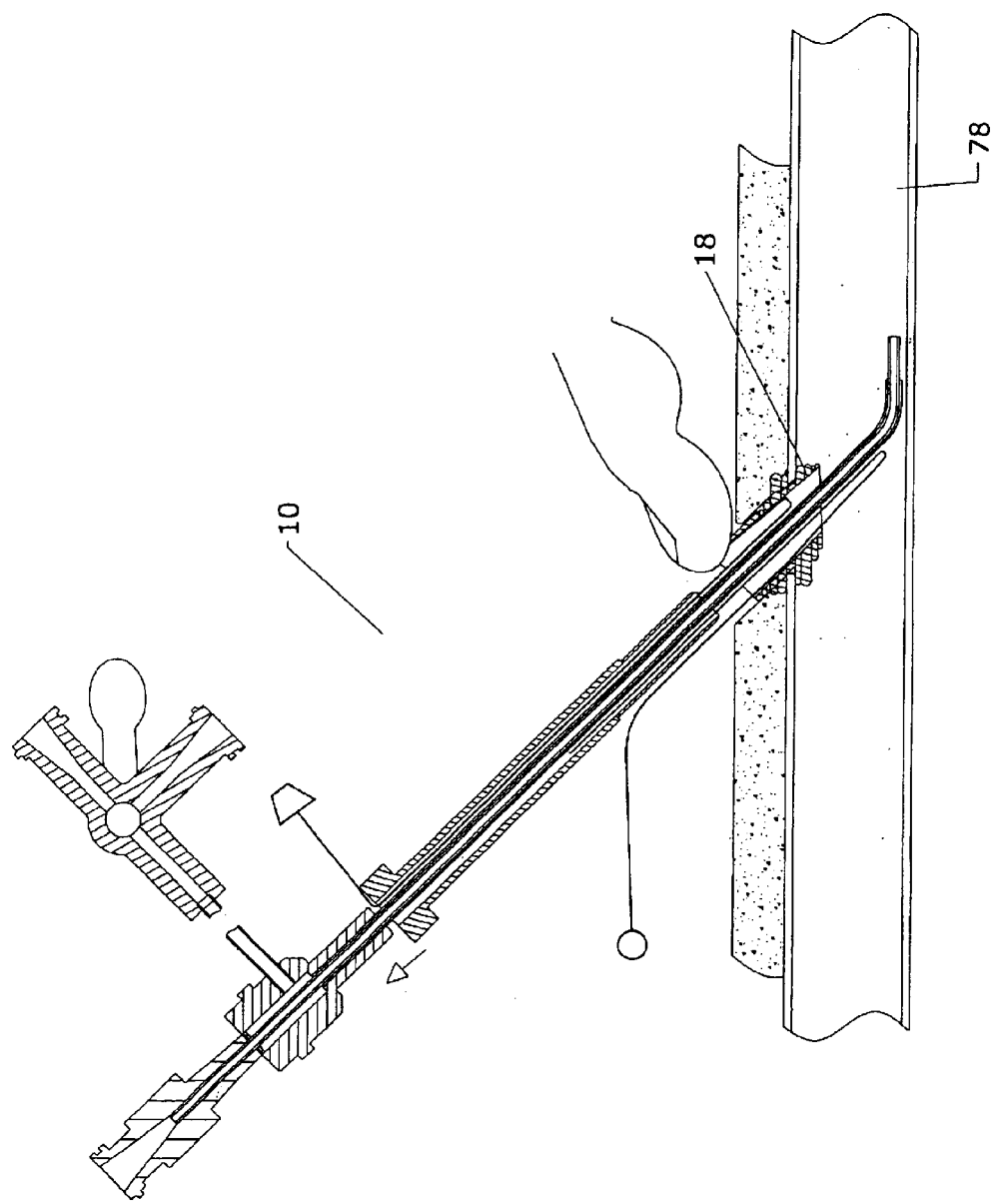

METHOD AND APPARATUS FOR SEALING ACCESS

CROSS-REFERENCE TO RELATED APPLICATIONS

This application claims priority under 35 U.S.C. § 119(e) to U.S. Provisional Application Serial No. 60/297,060, filed on Jun. 8, 2001.

FIELD OF THE INVENTION

The present invention relates to an apparatus and a method for sealing a puncture in a tubular tissue structure or the wall of a body cavity. More particularly, the present invention is directed to sealing a puncture site with submucosal tissue or another extracellular matrix-derived tissue capable of remodeling endogenous connective tissue.

BACKGROUND AND SUMMARY OF THE INVENTION

The control of bleeding during and after surgery is important to the success of the procedure. The control of blood loss is of particular concern if the surgical procedure is performed directly upon or involves the patient's arteries and veins. Well over one million surgical procedures are performed annually which involve the insertion and removal of catheters into and from arteries and veins. Accordingly, these types of vasculature procedures represent a significant amount of surgery in which the control of bleeding is of particular concern.

Typically, the insertion of a catheter creates a puncture through the vessel wall and upon removal the catheter leaves a puncture opening through which blood may escape and leak into the surrounding tissues. Therefore, unless the puncture site is closed clinical complications may result leading to increased hospital stays with the associated costs. To address this concern, medical personnel are required to provide constant and continuing care to a patient who has undergone a procedure involving an arterial or venous puncture to insure that post-operative bleeding is controlled.

Surgical bleeding concerns can be exacerbated by the administration of a blood thinning agent, such as heparin, to the patient prior to a catheterization procedure. Since the control of bleeding in anti-coagulated patients is much more difficult to control, stemming blood flow in these patients can be troublesome. A common method of healing the puncture to the vessel is to maintain external pressure over the vessel until the puncture seals by natural clot formation processes. This method of puncture closure typically takes about thirty to ninety minutes, with the length of time usually being greater if the patient is hypertensive or anti-coagulated.

Furthermore, it should be appreciated that utilizing pressure, such as human hand pressure, to control bleeding suffers from several drawbacks regardless of whether the patient is hypertensive or anti-coagulated. In particular, when human hand pressure is utilized, it can be uncomfortable for the patient, can result in excessive restriction or interruption of blood flow, and can use costly professional time on the part of the hospital staff. Other pressure techniques, such as pressure bandages, sandbags, or clamps require the patient to remain motionless for an extended period of time and the patient must be closely monitored to ensure the effectiveness of these techniques.

Other devices have been disclosed which plug or otherwise provide an obstruction in the area of the puncture (see, for example, U.S. Pat. Nos. 4,852,568 and 4,890,612) wherein a collagen plug is disposed in the blood vessel opening. When the plug is exposed to body fluids, it swells to block the wound in the vessel wall. A potential problem with plugs introduced into the vessel is that particles may break off and float downstream to a point where they may lodge in a smaller vessel, causing an infarct to occur. Another potential problem with collagen plugs is that there is the potential for the inadvertent insertion of the collagen plug into the lumen of the blood vessel which is hazardous to the patient. Collagen plugs also can act as a site for platelet aggregation, and, therefore, can cause intraluminal deposition of occlusive material creating the possibility of a thrombosis at the puncture sight. Other plug-like devices are disclosed, for example, in U.S. Pat. Nos. 5,342,393, 5,370,660 and 5,411,520.

Accordingly, there is a need for surgical techniques suitable for sealing punctures in a tubular tissue structure or in the punctured wall of a body cavity, such as a heart chamber, or a body cavity of another organ. Such techniques require rapid, safe, and effective sealing of the puncture. It would also be advantageous to close the puncture without disposing any occlusive material into the vessel or body cavity, and without introducing infectious organisms into the patient's circulatory system.

The present invention is directed to an apparatus and method for sealing punctured tubular tissue structures, including arteries and veins, such as punctures which occur during diagnostic and interventional vascular and peripheral catheterizations, or for sealing a puncture in the wall of a body cavity. More specifically, the apparatus and method of the present invention employ submucosal tissue or another extracellular matrix-derived tissue to seal punctures in tubular tissue structures, such as blood vessels, or in the wall of a body cavity. The submucosal tissue or other extracellular matrix-derived tissue is capable of inducing tissue remodeling at the site of implantation by supporting the growth of connective tissue in vivo, and has the added advantages of being tear-resistant so that occlusive material is not introduced into the patient's circulatory system. Also, submucosal tissue or another extracellular matrix-derived tissue has the advantage of being resistant to infection, thereby reducing the chances that the procedure will result in systemic infection of the patient.

In one embodiment, a method of sealing a puncture site in the wall of a tubular tissue structure is provided. The method comprises the step of inserting submucosal tissue of a warm-blooded vertebrate into the puncture site.

In another embodiment a method of sealing a puncture site in the wall of a body cavity is provided. The method comprises the step of inserting submucosal tissue of a warm-blooded vertebrate into the puncture site.

In an alternate embodiment a method of sealing a puncture site in the wall of a tubular tissue structure is provided. The method comprises the step of inserting an intact extracellular matrix-derived tissue of a warm-blooded vertebrate into the puncture site.

In another embodiment a method of sealing a puncture site in the wall of a body cavity is provided. The method comprises the step of inserting an intact extracellular matrix-derived tissue of a warm-blooded vertebrate into the puncture site.

In another embodiment, a method of sealing a puncture site in the wall of a tubular tissue structure or in the wall of a body cavity is provided. The method comprises the steps of (a) inserting an introducer element into the puncture site, the introducer element having a sheet comprising submucosal tissue or another extracellular matrix-derived tissue of a warm-blooded vertebrate, the sheet having a user distal end and a user proximal end, wherein the proximal end of the sheet remains outside of the punctured wall and the distal end of the sheet is inserted into the tubular tissue structure or the body cavity, and wherein the sheet has at least one tether for positioning the distal end relative to the puncture site, (b) pulling the tether to position the distal end of the sheet relative to the puncture site, and (c) pulling the tether to position the distal end of the sheet within the puncture site.

In yet another embodiment an apparatus for sealing a puncture site in the wall of a tubular tissue structure or in the wall of a body cavity in a patient is provided. The apparatus comprises an introducer element and a sheet of submucosal tissue or another extracellular matrix-derived tissue on the introducer element, the sheet having a user distal end and a user proximal end.

In an alternate embodiment, a tissue graft for sealing a puncture site in the wall of a tubular tissue structure or in the wall of a body cavity is provided. The tissue graft comprises submucosal tissue or another extracellular matrix-derived tissue and at least one tether attached to the tissue graft.

In another embodiment, an apparatus for sealing a puncture site in the wall of a tubular tissue structure or in the wall of a body cavity in a patient is provided. The apparatus comprises an introducer element, a positioning tube positioned on the introducer element, to provide at least one lumen for containing a retaining tether, a sheet of submucosal tissue or another extracellular matrix-derived tissue positioned on the positioning tube, the sheet having a user distal end and a user proximal end, and at least one tether attached at or near the distal end of the sheet for positioning the distal end of the sheet relative to the puncture site.

In still another embodiment, an apparatus for containing a tether is provided. The apparatus comprises a tubular spacer element for positioning on an introducer element, the spacer element having an inner surface and an outer surface, and at least one ridge on the inner surface of the spacer element to prevent the inner surface of the spacer element from contacting the introducer element to provide at least one lumen for containing the tether.

In another embodiment, an apparatus for containing a tether is provided. The apparatus comprises a tubular spacer element having an inner surface, an outer surface, and at least one lumen positioned between the inner and outer surfaces to provide at least one lumen to contain the tether.

In yet another embodiment a kit is provided. The kit comprises an introducer element and a sheet of submucosal tissue or another extracellular matrix-derived tissue.

DETAILED DESCRIPTION OF THE INVENTION

Figure 1A:
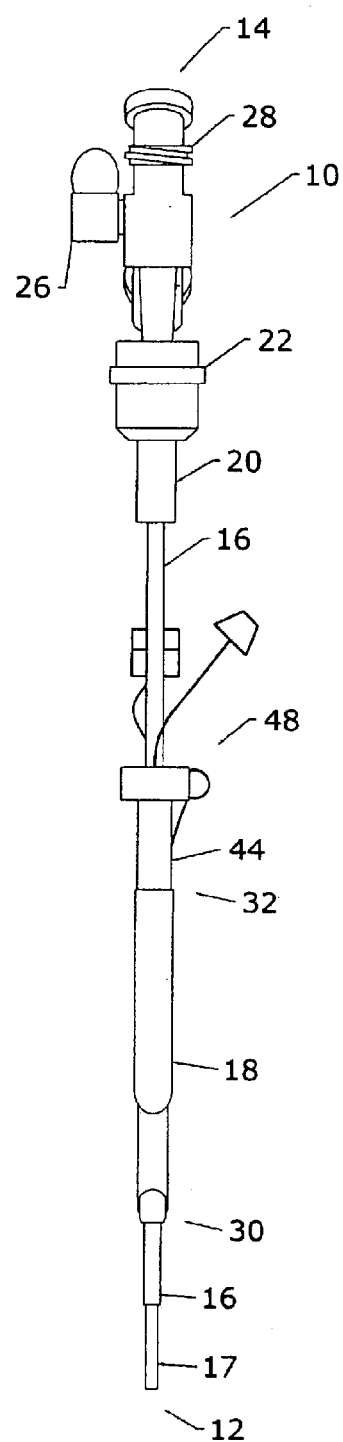
FIGS. 1 A–I illustrate introducer elements for use in sealing access to a tubular tissue structure or a body cavity.
Figure 1B:
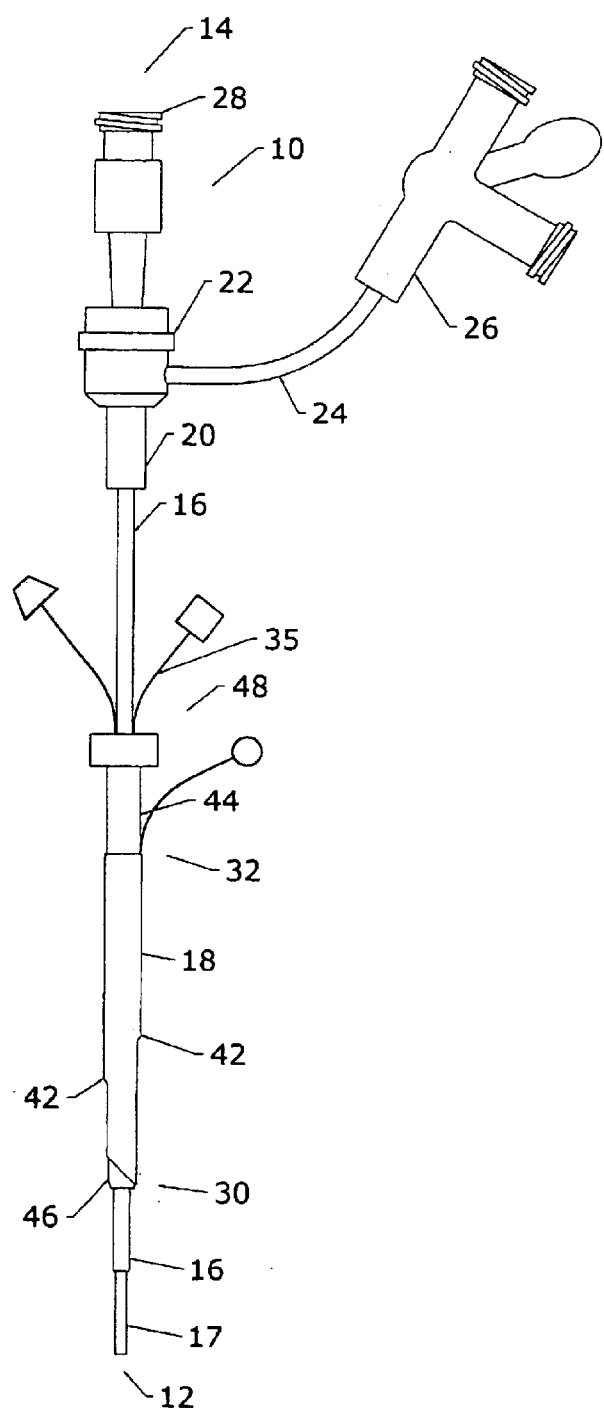
Figure 1C:
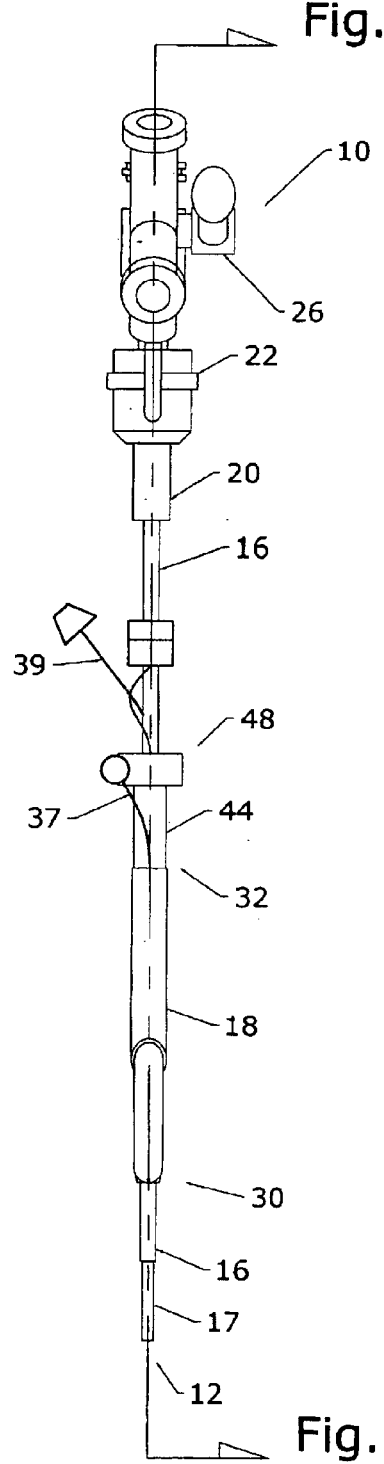
Figure 1D:
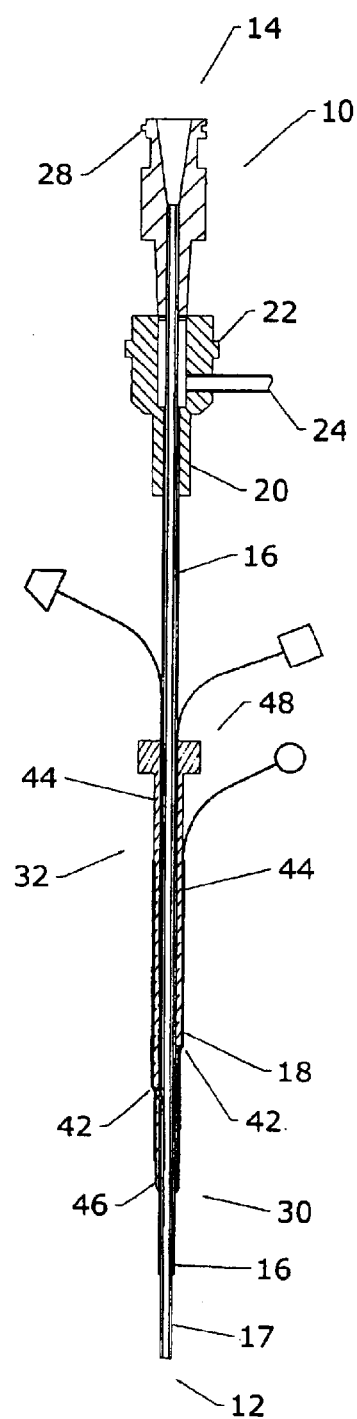

The present invention is related to an apparatus and a method for sealing a puncture in a tubular tissue structure, such as a blood vessel, or in the wall of a body cavity, with submucosal tissue or another extracellular matrix-derived tissue capable of supporting the growth of endogenous connective tissue in vivo resulting in remodeling of endogenous connective tissue at the puncture site and in formation of a static seal. The apparatus and method of the present invention can be used to seal a puncture in a tubular tissue structure, such as a blood vessel, or in the wall of a body cavity, that has been created intentionally or unintentionally during a surgical procedure or nonsurgically (e.g., during an accident). Punctures made intentionally include vascular punctures made in various types of vascular, endoscopic, or orthopaedic surgical procedures, or punctures made in any other type of surgical procedure, in coronary and in peripheral arteries and veins or in the wall of a body cavity. Such procedures include angiographic examination, angioplasty, laser angioplasty, valvuloplasty, atherectomy, stent deployment, rotablator treatment, aortic prosthesis implantation, intraortic balloon pump treatment, pacemaker implantation, any intracardiac procedure, electrophysiological procedures, interventional radiology, and various other diagnostic, prophylactic, and therapeutic procedures such as dialysis and procedures relating to percutaneous extracorporeal circulation.

Referring now to the drawings, FIG. 1 illustrates an introducer 10 adapted for catheterization, exemplary of the type of introducer element that may be used in accordance with the present invention. Although an introducer 10 adapted for use in catheterization procedures is illustrated in FIG. 1, it is understood that the present invention is applicable to any type of introducer element used to provide access to the lumen of a tubular tissue structure, such as a blood vessel, or to a body cavity. For example, the present invention is applicable to an introducer element such as a needle, a cannula, a guide wire, an introducer element adapted for dialysis, a trocar, or any other introducer element used to access the lumen of a tubular tissue structure or a body cavity.

An introducer 10 as depicted in FIG. 1 can be used when performing catheterization procedures in coronary and peripheral arteries and veins. Typically, a catheter is introduced into the vascular system by first penetrating the skin, underlying muscle tissue, and the blood vessel with a needle, and a guide wire is inserted through the lumen of the needle and enters the blood vessel. Subsequently, the needle is stripped off the guide wire and an introducer 10 is fed over the guide wire and pushed through the skin and through the vessel wall to enter the vessel. The guide wire can then be removed and a catheter is fed through the lumen of the introducer 10 and advanced through the vascular system until the working end of the catheter is positioned at a predetermined location. Alternatively, the guide wire may be left in place throughout the procedure and the introducer 10 removed before the guide wire is removed. At the end of the catheterization procedure, the catheter is withdrawn. The introducer 10 is also removed and the opening through which, for example, the introducer 10 is inserted must be sealed as quickly as possible once the procedure is completed. Although a typical catheterization procedure utilizing an introducer 10 is described, the described procedure is non-limiting. Furthermore any embodiment of the introducer 10 described below is applicable to any other introducer element for use in accessing the lumen of a tubular tissue structure or a body cavity in accordance with the invention.

The present invention may be employed, for example, to rapidly seal a puncture site in a blood vessel upon completion of a catheterization procedure. The introducer 10 illustrated in FIGS. 1A–I is an exemplary embodiment and has a user distal end 12 for insertion into a blood vessel and a user proximal end 14. A standard introducer comprises a dilator 17 and a sheath 16 which extends axially over the dilator 17, a sheath cap 20 disposed axially over a portion of the sheath 16 and a valve cap 22 connected to the sheath cap 20 and to a side port tube 24. A standard introducer may also comprise a three-way valve 26 connected to an end of the side port tube 24, and a syringe connector 28, adapted for the attachment of a syringe to the introducer 10 and connected to the valve cap 22. Although not part of a standard introducer, the introducer 10 depicted in FIG. 1 further comprises a positioning tube 44 which extends axially over a portion of the sheath 16, and a sheet 18 of submucosal tissue or another extracellular matrix-derived tissue extending axially over a portion of the positioning tube 44.

Figure 1E:
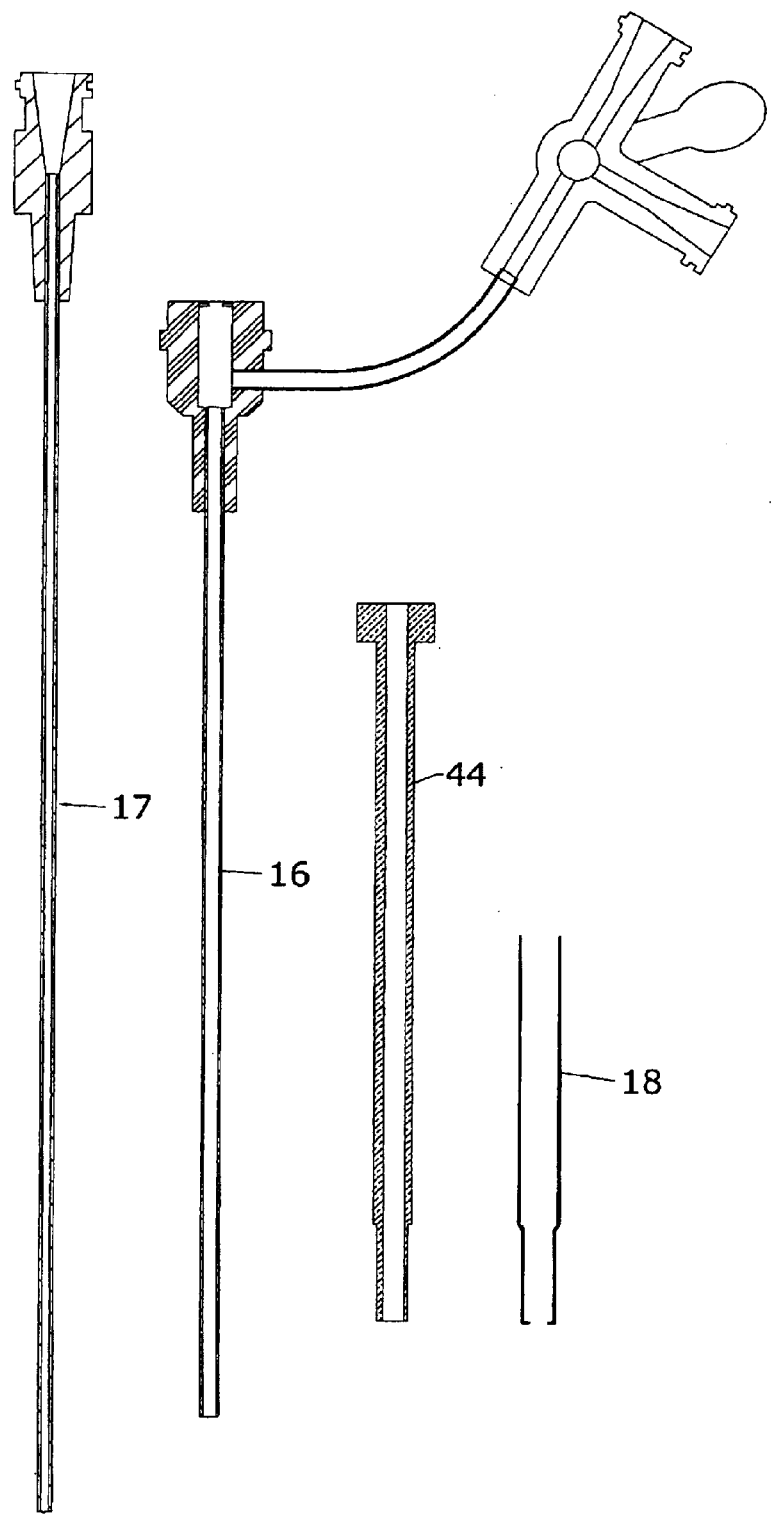
Figure 1F:
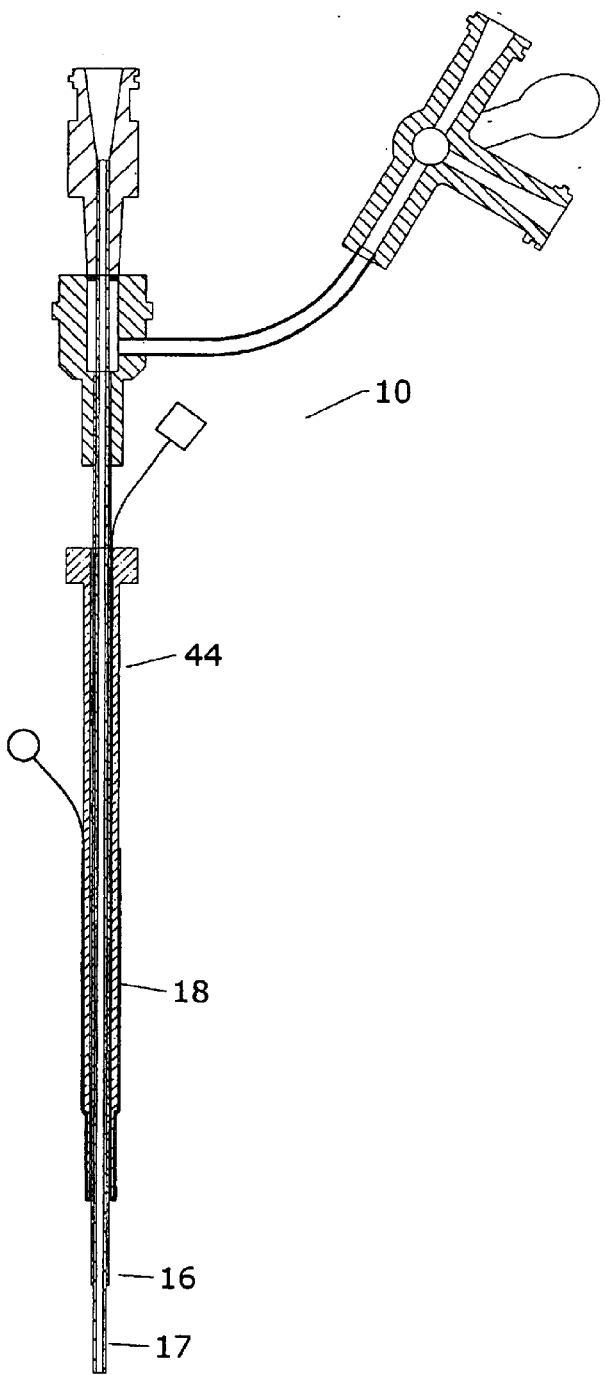
Figure 1G:
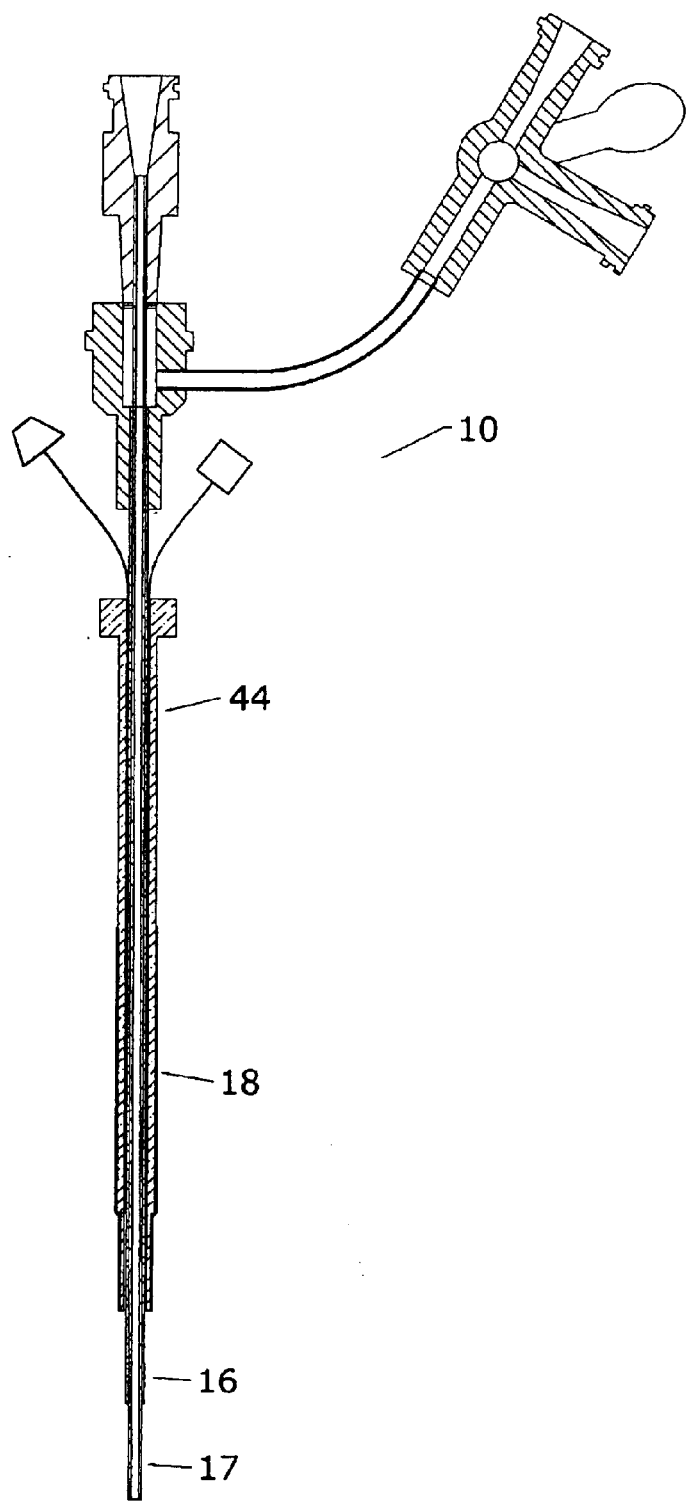
Figure 1H:
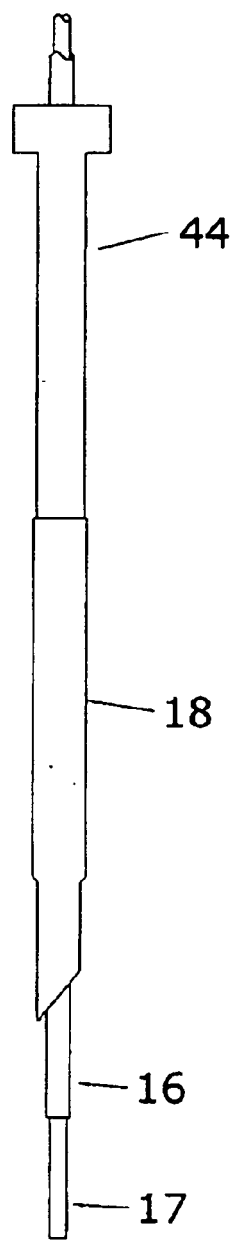
Figure 1I:
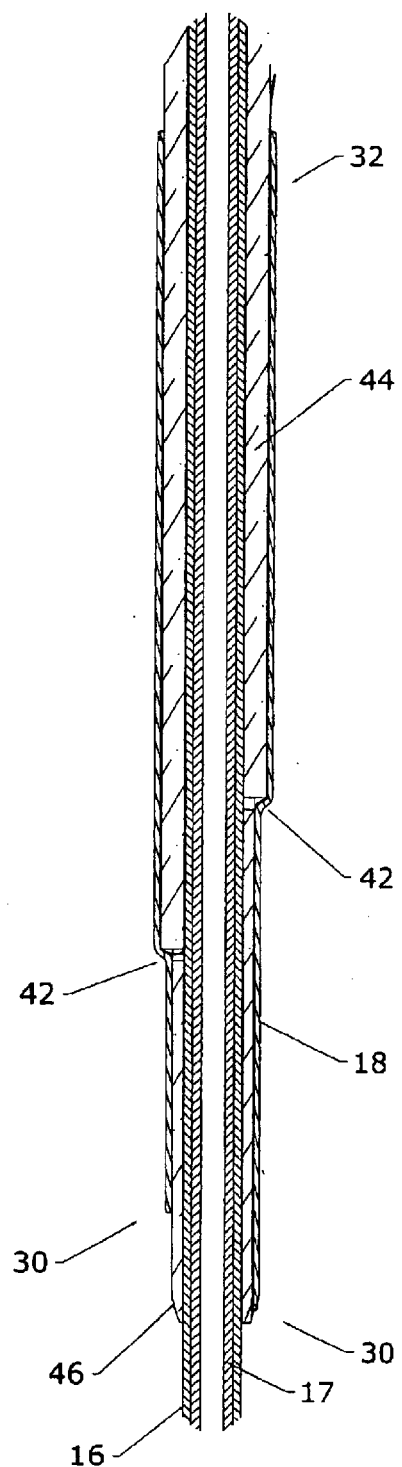
Figure 2A:
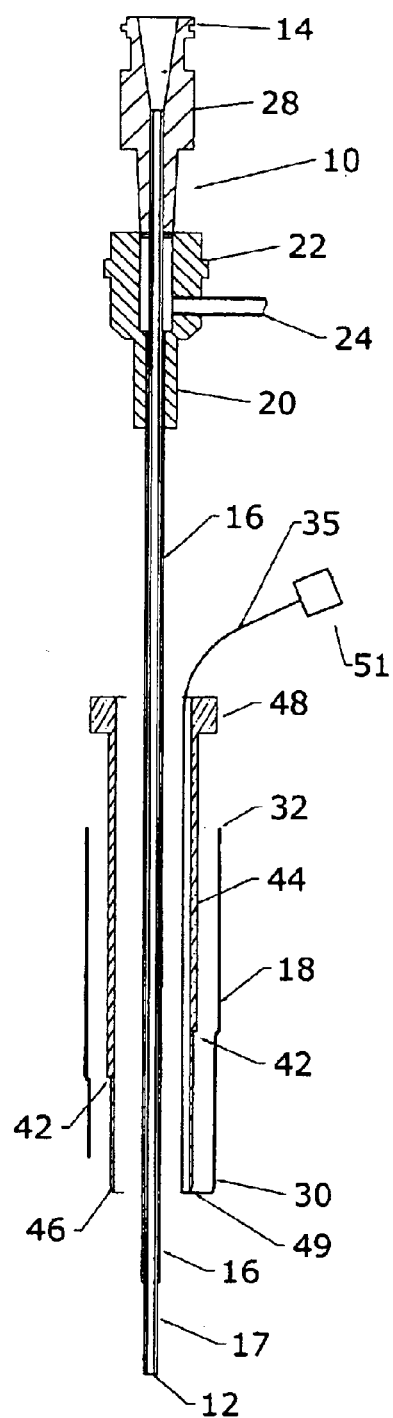
FIGS. 2 A–I illustrate various tether configurations on introducer elements for use in sealing access to a tubular tissue structure or a body cavity.
Figure 2B:
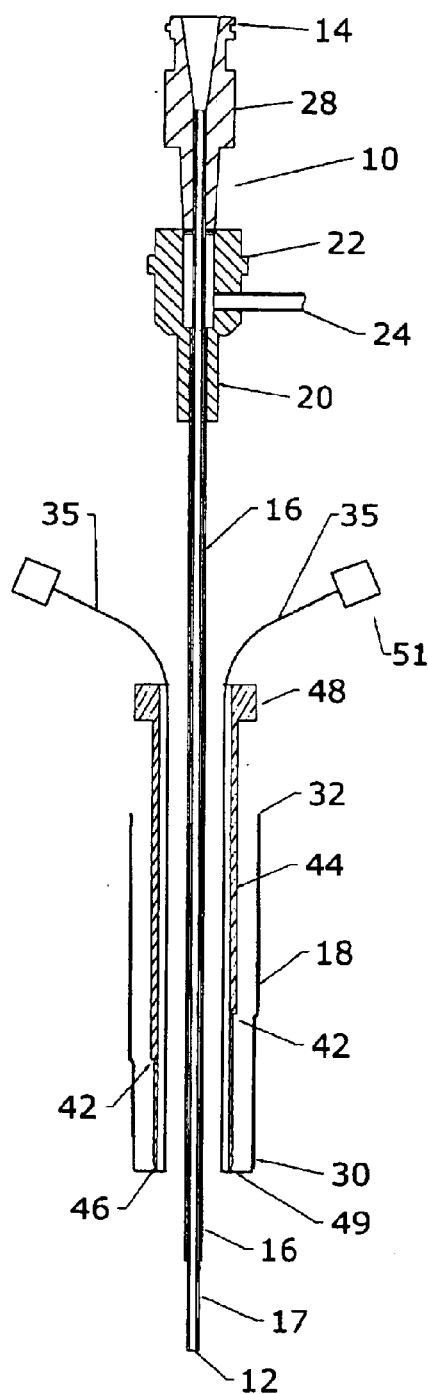
Figure 2C:
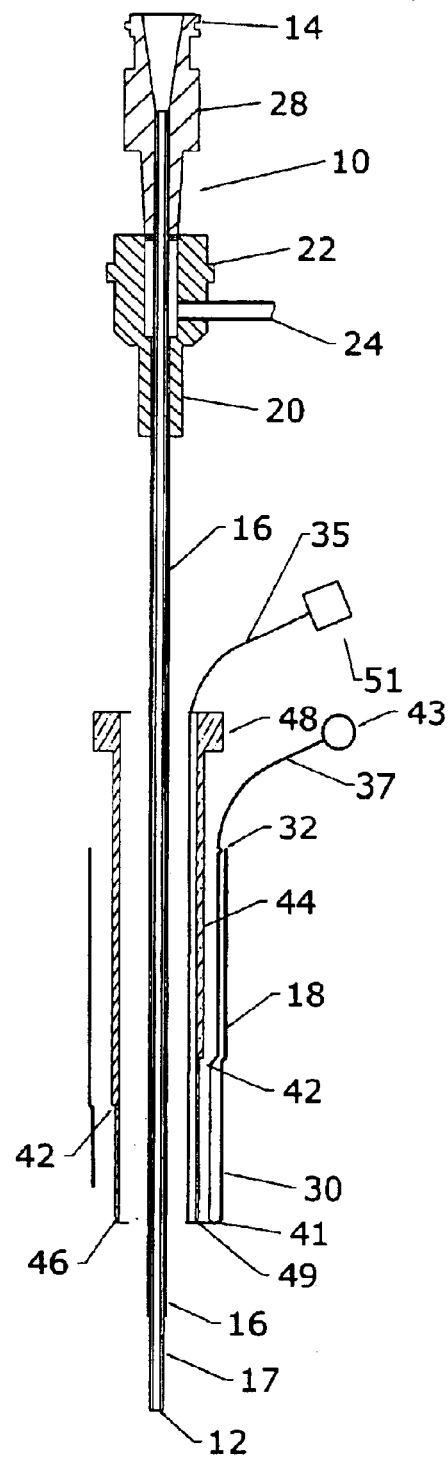
Figure 2D:
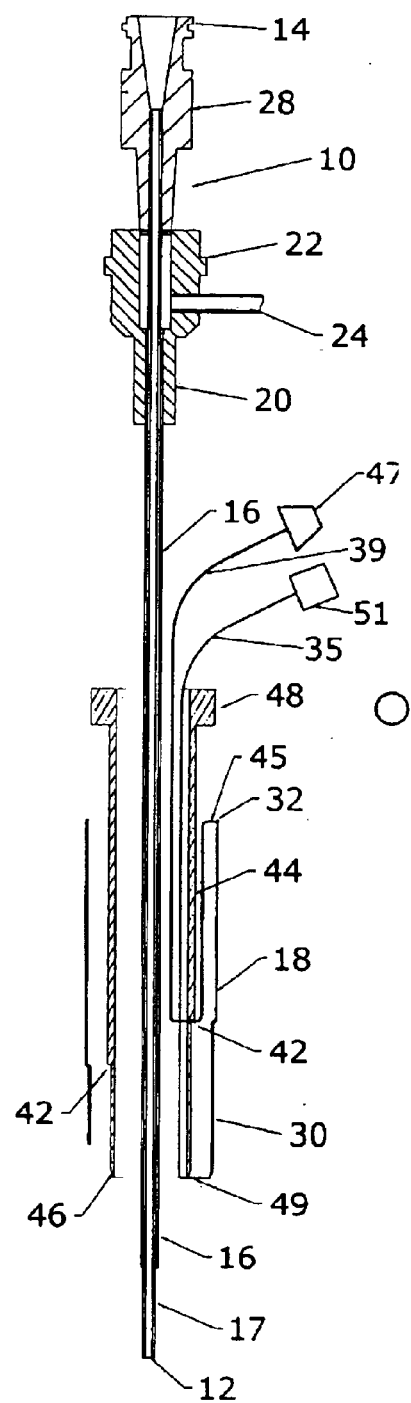
Figure 2E:
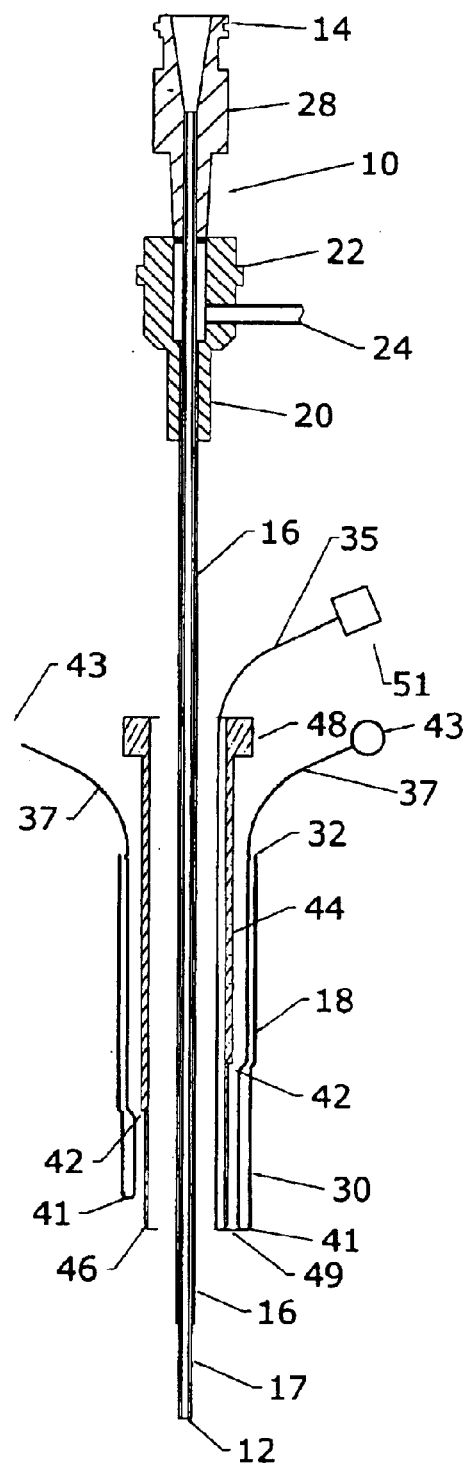
Figure 2F:
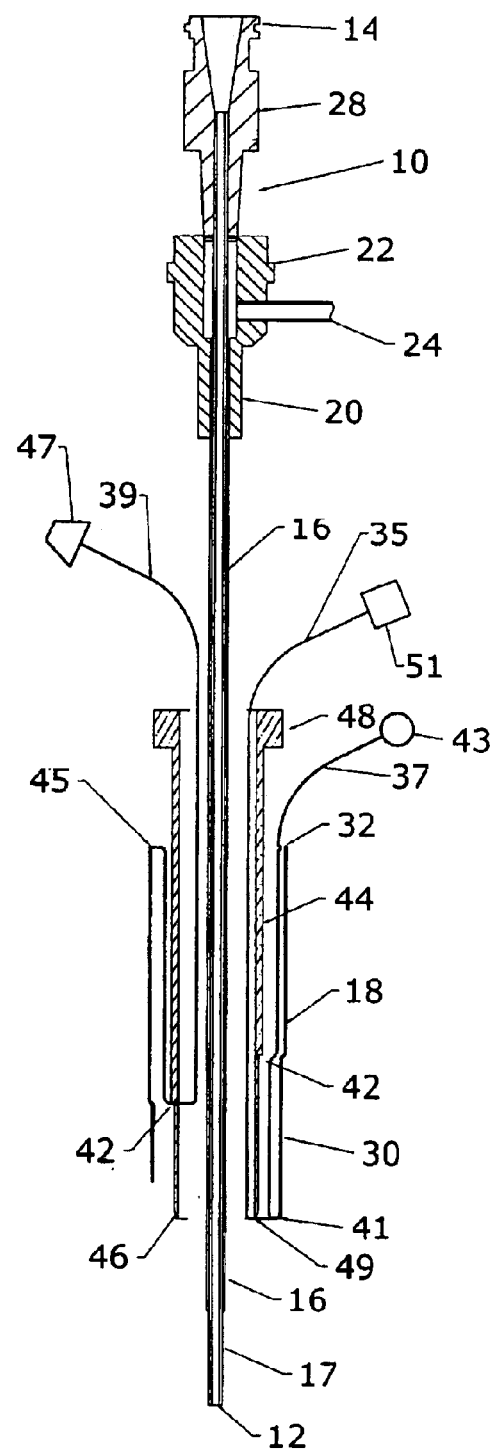
Figure 2G:
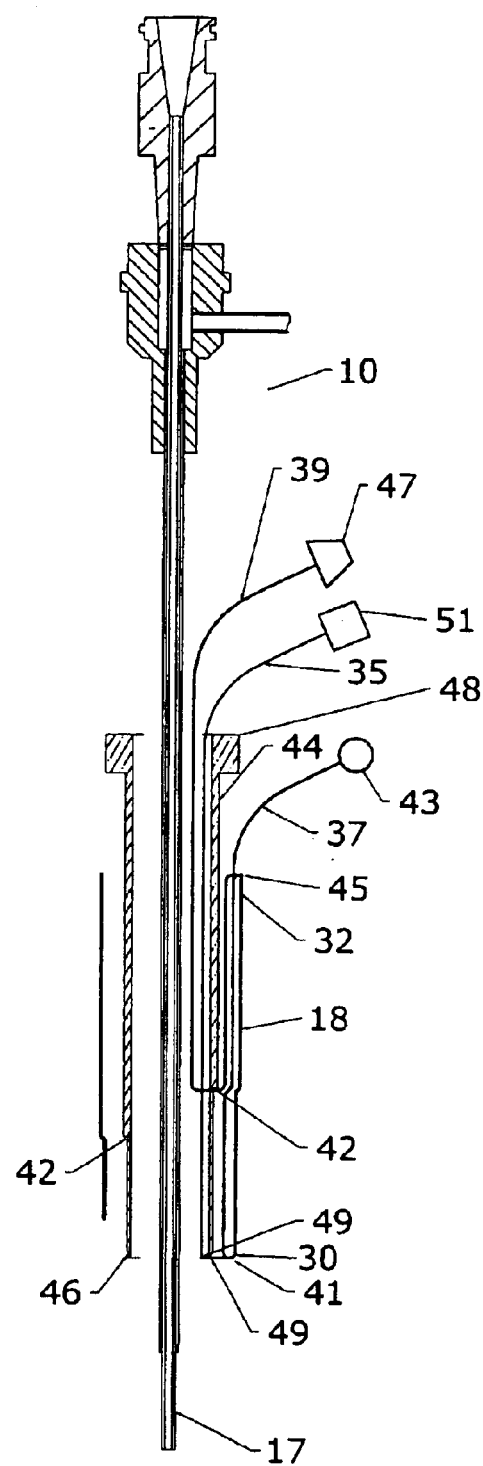
Figure 2H:
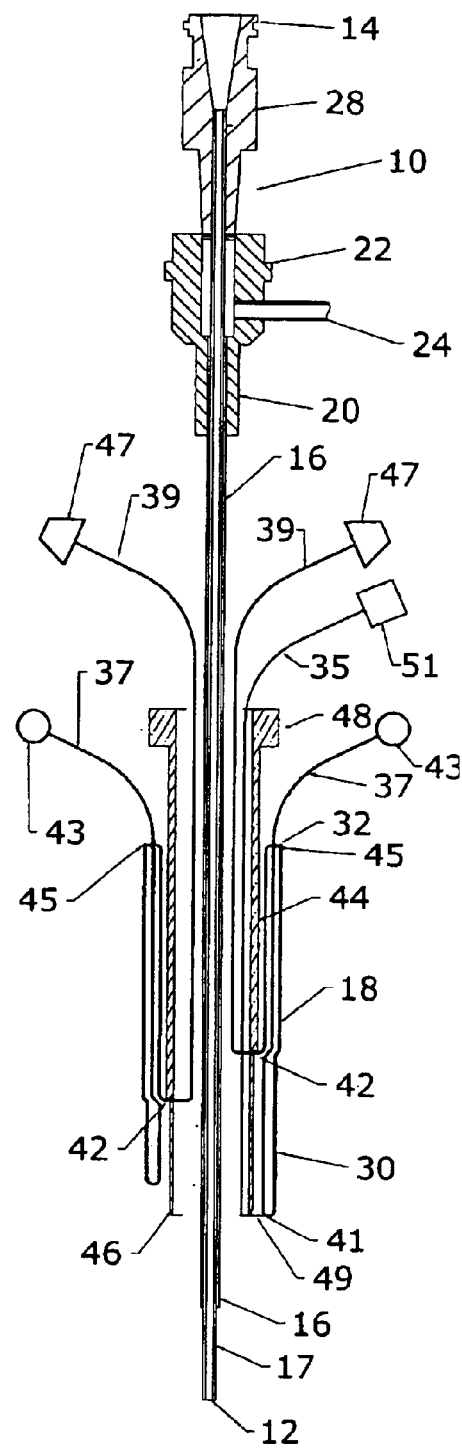
Figure 2I:
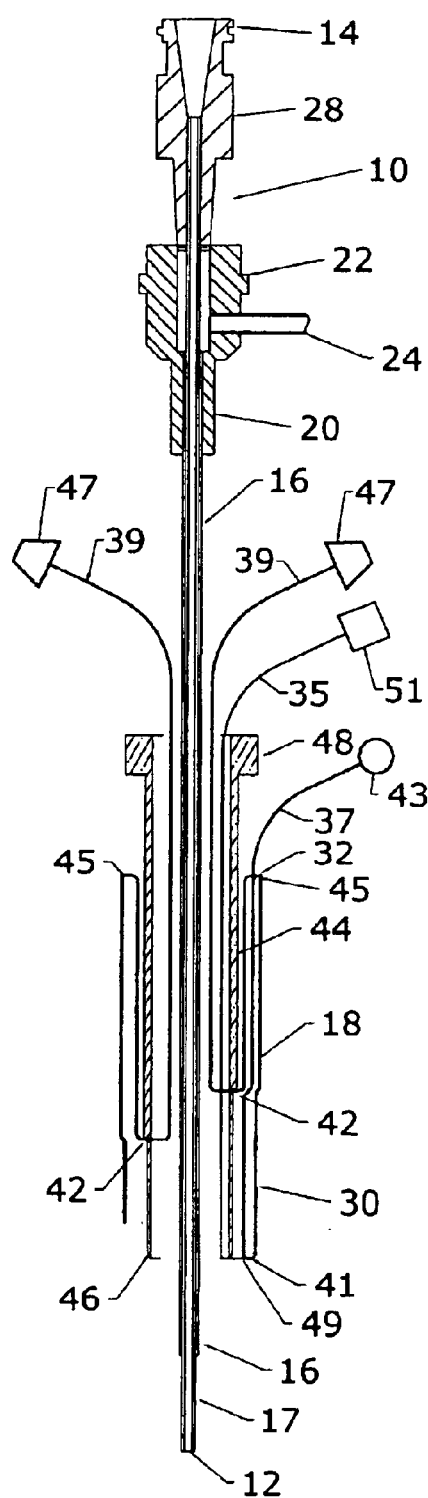
Figure 2J:
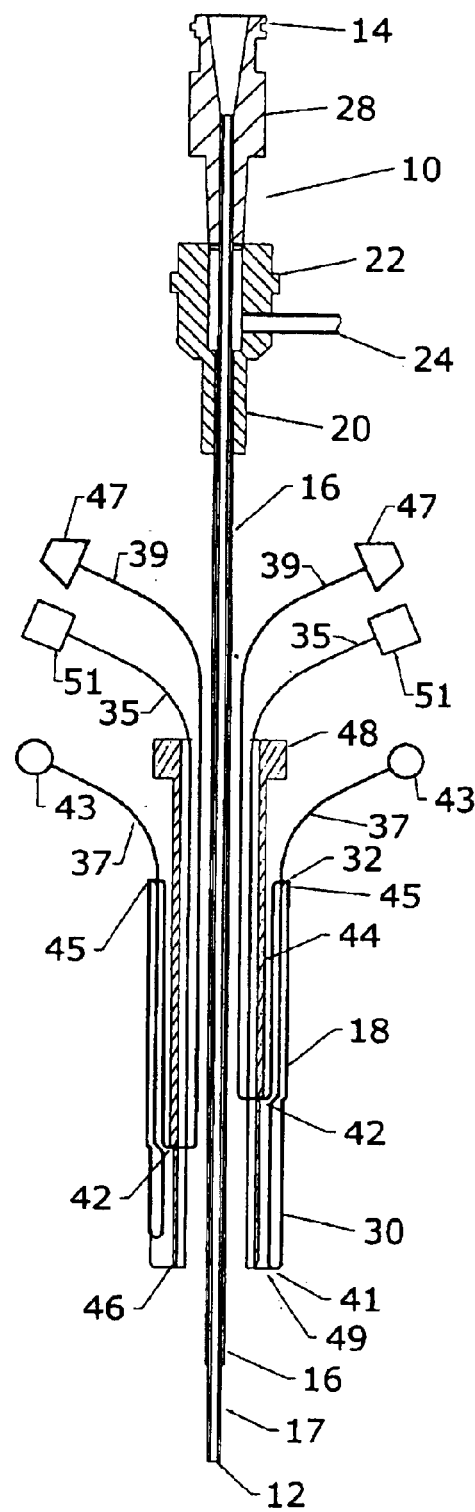

In the embodiment of the invention depicted in FIG. 1 (see FIG. 1B), a sheet 18 of submucosal tissue or another extracellular matrix-derived tissue extends axially over a portion of the positioning tube 44 (described in more detail below), and the positioning tube 44 extends axially over the sheath 16. FIGS. 1E–G depicts the sheath 16, the dialator 17, the positioning tube 44, and the sheet 18 in a disassembled cross-sectional form, and assembled to construct an introducer 10. The sheet 18 has a user distal end 30 which is inserted into a tubular tissue structure, such as a blood vessel, and a user proximal end 32 which remains outside of the punctured vessel wall. The proximal end 32 of the sheet 18 may extend axially over a portion of the introducer 10 as depicted in FIG. 1 or may extend to and be held in place by the sheath cap 20.

In embodiments where the user proximal end 32 of the sheet 18 does not extend to the sheath cap 20, the user proximal end 32 of the sheet 18 may be held in place, for example, by a string attached to the user proximal end 32 of the sheet 18 and the sheath cap 20 or the valve cap 22. As a result, the sheet 18 is prevented from being pushed down the introducer 10 when the user inserts the introducer 10 through, for example, a vessel wall with his hand in contact with the sheet 18. The string may be cut to allow the user proximal end 32 of the sheet 18 to be gathered externally to seal the puncture site as described below. In other embodiments, the user proximal end 32 of the sheet 18 or other parts of the sheet 18 may be held in place by metal or plastic clamps, O-rings, or the like, which may be removed from the end of the sheet 18 when it is necessary to gather the sheet 18 externally to seal the puncture site. Alternatively, as shown in FIG. 1, the sheet 18 may extend axially over only a portion of the introducer 10 so that the proximal end 32 of the sheet 18 is distal to the points at which the hand of the user contacts the introducer 10 and does not come in contact with the hand of the user when the introducer 10 is being inserted through the vessel wall. The sheet 18 can be of any length (e.g., in the form of a disk), as long as the sheet 18 is of sufficient length to plug the puncture site in the vessel wall or in the wall of a body cavity.

Figure 10A:
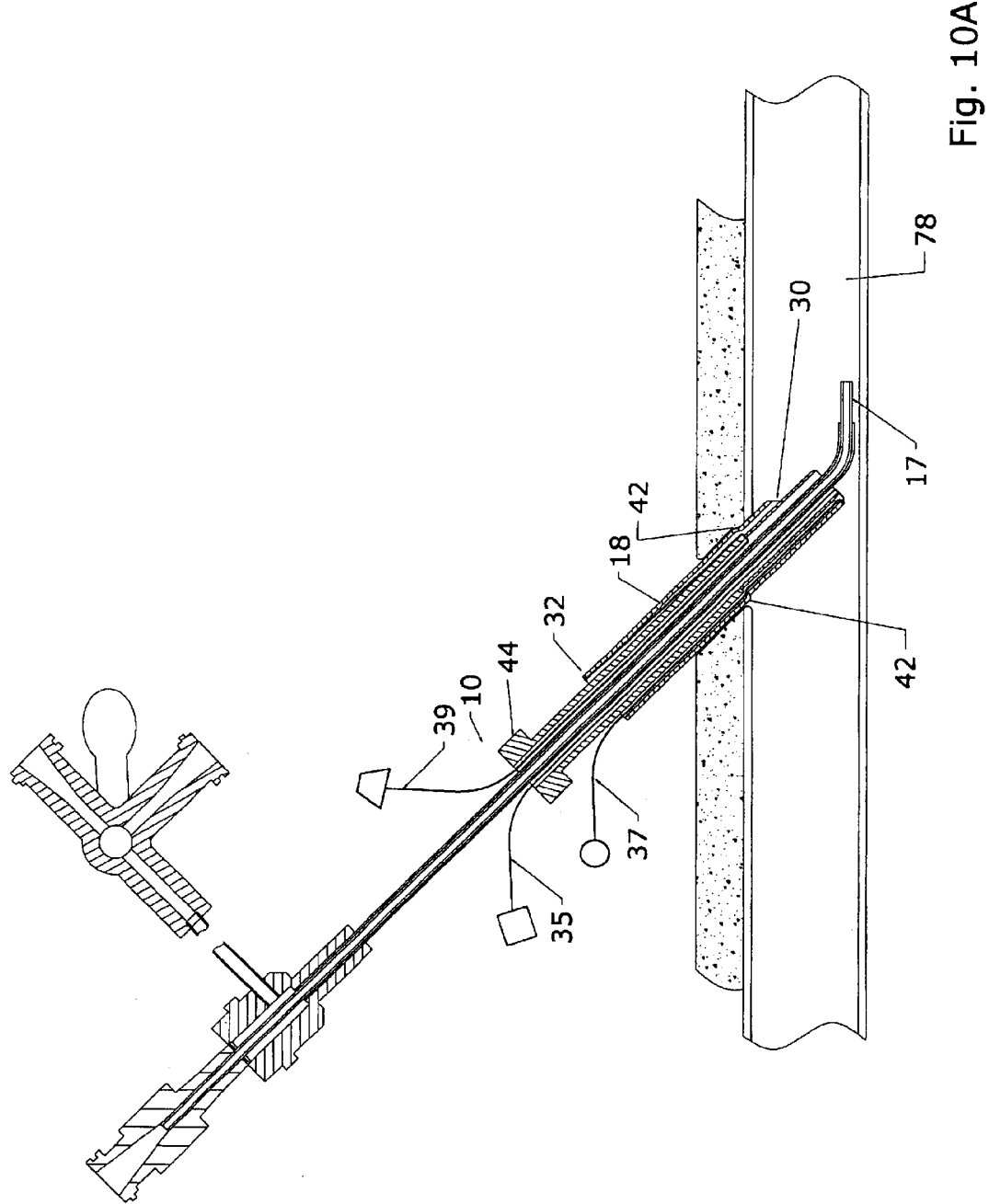
FIGS. 10 A–G illustrate a method of sealing access to a tubular tissue structure or a body cavity.

As also depicted in FIG. 1 (see FIG. 1B), in one embodiment the user distal end 30 of the sheet 18 is tapered from the user distal end 30 towards the user proximal end 32 to prevent the sheet 18 from rolling up the introducer 10 upon insertion into the blood vessel when the sheet 18 is positioned, as shown in FIG. 10A during insertion into the blood vessel. Although, a sheet 18 tapered at the user distal end 30 is depicted in FIG. 1, any configuration of the user distal end 30 of the sheet 18 can be used which prevents the sheet 18 from rolling up the introducer 10 upon insertion into the blood vessel.

As shown in FIGS. 1 and 2, the sheet 18 has at least one or more tethers 35, 37 attached at or near to the distal end 30 of the sheet 18 and at least one tether 39 attached at or near the proximal end 32 of the sheet 18. For example, as depicted in FIG. 2G one or more pull-up tethers 37 may be attached at or near to the distal end 30 of the sheet 18, and one or more pull-down tethers 39 may be attached at or near to the proximal end 32 of the sheet 18. As also depicted in FIG. 2, one or more retaining tethers 35 may be attached at or near to the distal end 30 of the sheet 18. The function of the various types of tethers is described below.

The pull-up tether 37 is attached to the sheet 18 at or near the distal end 30 of the sheet 18 and extends axially upwards towards the proximal end 32 of the sheet 18 between the positioning tube 44 and the sheet 18. Thus, the distal end 41 of the pull-up tether is inserted into the blood vessel when the introducer 10 is pushed through the vessel wall and the proximal end 43 of the pull-up tether 37 remains externally exposed. Upon completion of the procedure, such as catheterization, the proximal end 43 of the pull-up tether 37 is pulled to gather the distal end 30 of the sheet 18 in the puncture site from the inside of the vessel wall (see FIGS. 10C–D).

The pull-down tether 39 is attached at or near the proximal end 32 of the sheet 18 and extends axially downwards between the sheet 18 and the positioning tube 44 towards the distal end 46 of the positioning tube 44. The pull-down tether 39 further extends radially inwards under the positioning tube 44 and then extends axially upwards between the positioning tube 44 and the sheath 16 towards the proximal end 48 of the positioning tube 44. Thus, the attached end 45 and the unattached end 47 of the pull-down tether 39 remain externally exposed when the introducer 10 is inserted into the blood vessel wall. Upon completion of the procedure the unattached end 47 of the pull-down tether is pulled to gather the proximal end 32 of the sheet 18 in the puncture site from the outside of the vessel wall (see FIGS. 10D–E).

In one embodiment of the invention, a retaining tether 35 is attached (see FIG. 2G) to the distal end 30 of the sheet 18. As is described in more detail below with reference to FIG. 5, the distal end 49 of the retaining tether 35 is attached at or near the distal end 30 of the sheet 18. The retaining tether 35 extends axially upwards towards the proximal end 48 of the positioning tube 44 between the sheath 16 and the positioning tube 44. The distal end 49 of the retaining tether 35 is inserted into the blood vessel when the introducer 10 is pushed through the vessel wall. The proximal end 51 of the retaining tether 35 remains externally exposed. The function of the retaining tether is described below with reference to FIG. 5.

Preferably the present invention has one or more retaining tethers 35, one or more pull-up tethers 37, and one or more pull-down tethers 39. However, the invention may have any combination of pull-up tethers 37, pull-down tethers 39, and retaining tethers 35, or may lack one or more types of tethers. For example, the invention may lack a retaining tether 35 or a pull-down tether 39. Exemplary combinations of tethers are shown in FIG. 2A–J, but these combinations are not limiting.

Tethers with different functions (i.e., the retaining tether 35, the pull-up tether 37, and the pull-down tether 39) may have different indicia disposed thereon, such as different colors, so that the user can easily identify the tether with the desired function. Alternatively, tethers with different functions may have different caps attached to the externally exposed ends as shown in FIGS. 1–4 and 9–10 so that the tether with the desired function can be easily identified. The tethers are preferably made of resorbable thread and the tethers can be attached to the sheet 18 by any suitable means. For example, the tethers can be tied to the sheet 18 or hooked to the sheet 18 by using hooks, barbs, etc. (e.g., for tethers with attachment points that remain externally exposed when the introducer 10 is inserted into the vessel wall).

In one embodiment of the invention the positioning tube 44 (see FIGS. 1–4 and 10) extends axially over a portion of the sheath 16 and is positioned beneath the sheet 18. In another embodiment, the positioning tube 44 is disposed between a tubular spacer element 50, described below, and the sheet 18. The positioning tube 44 is used to insert the sheet 18 into the tubular tissue structure to a predetermined position relative to the sheet 18 (see FIGS. 10A–E). The positioning tube 44 has a user distal end 46, a user proximal end 48, and a tapered ledge 42 (see FIG. 1 I). As the user is inserting the introducer 10 with the sheet 18 through the wall of the tubular tissue structure the user feels resistance when the tapered ledge 42 of the positioning tube 44 reaches the outside of the wall of the tubular tissue structure. Accordingly, the resistance to insertion of the introducer 10 with the sheet 18 into the tubular tissue structure indicates to the user that the sheet 18 has been inserted to the desired, predetermined position relative to the sheet 18. Thus, the tapered ledge 42 of the positioning tube 44 functions as a tactile stop. The positioning tube 44 is exemplary of a mechanism that can be used to insert the sheet 18 into the tubular tissue structure or a body cavity to a predetermined position and other mechanisms can be used such as, for example, a positioning knot in the sheet 18 itself.

Figure 4A:
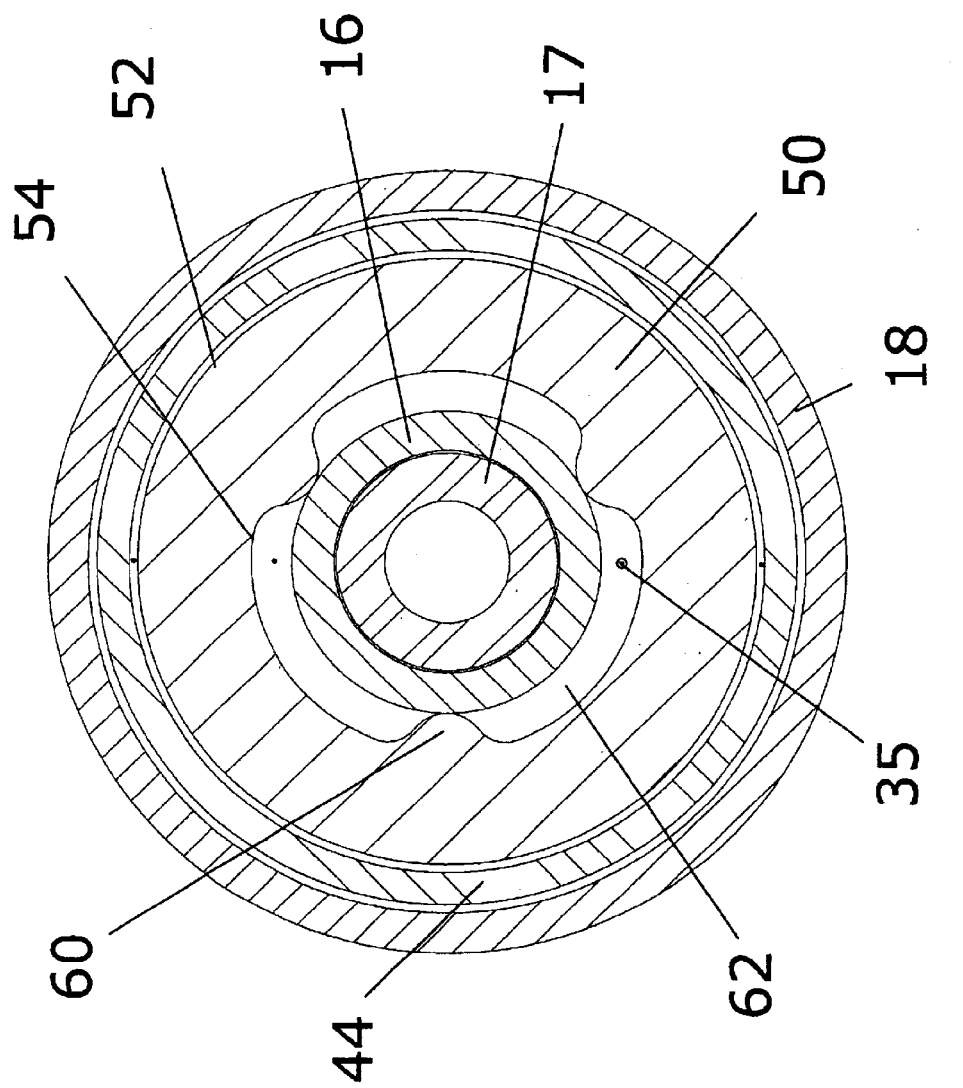
FIGS. 4 A–C illustrate views of various embodiments of a tubular spacer element.
Figure 4B:
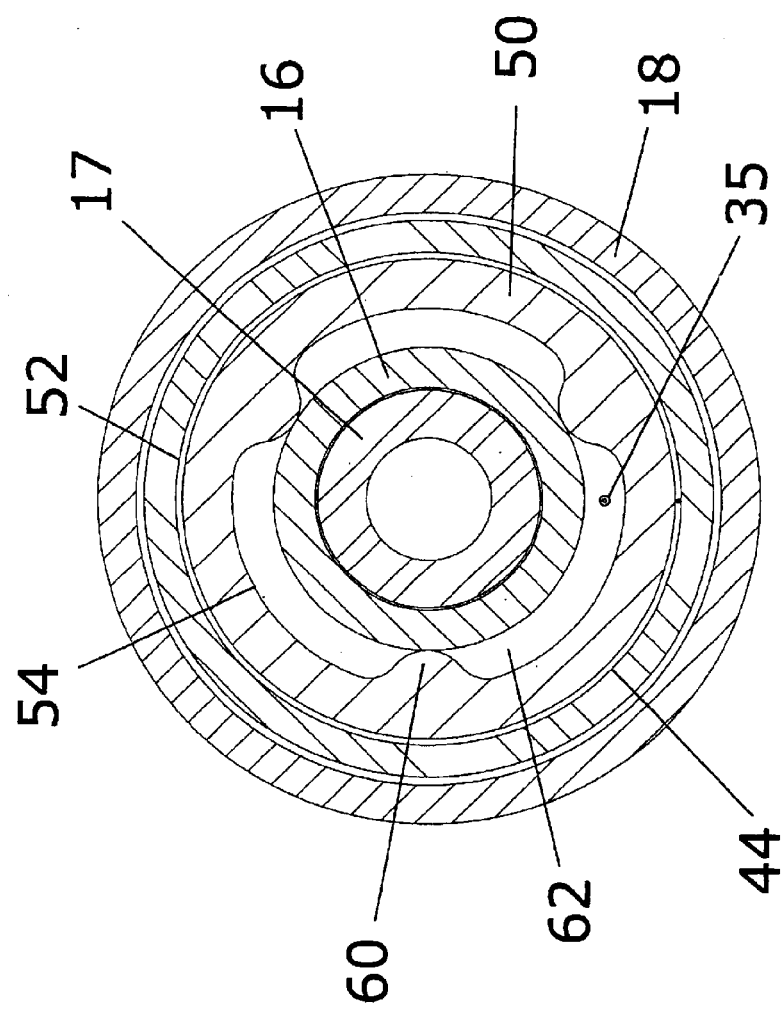
Figure 4C:
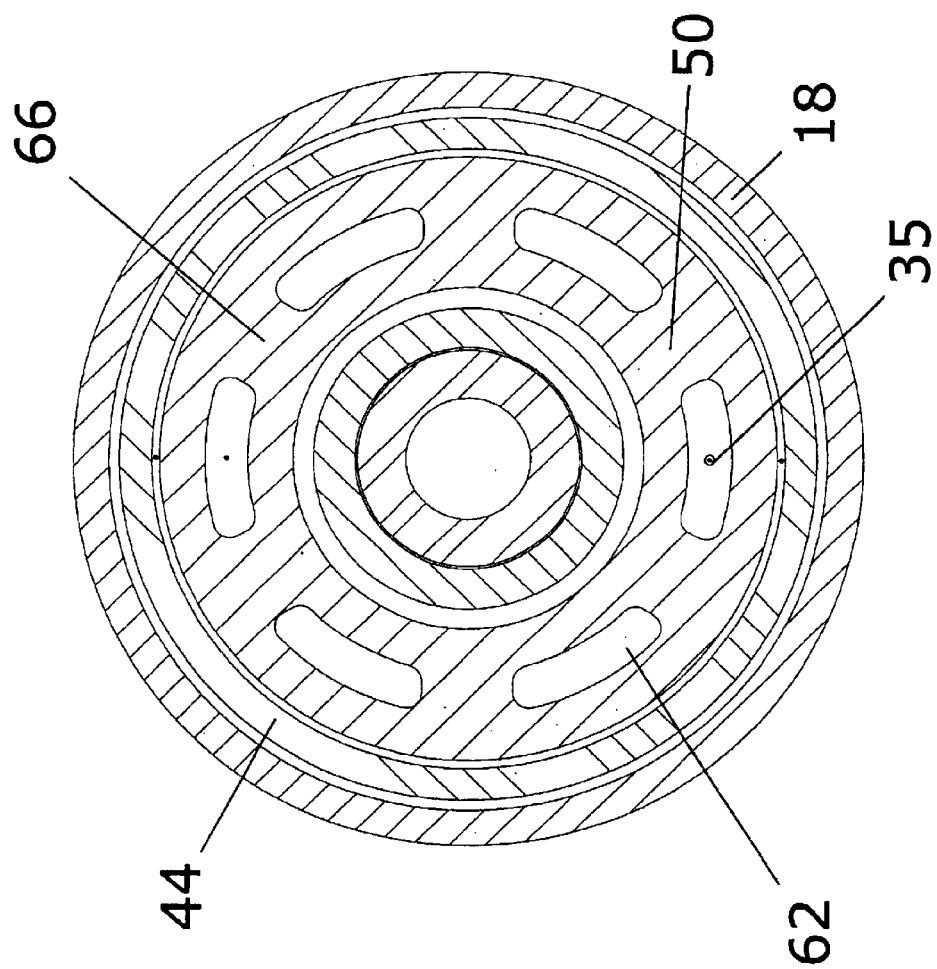
Figure 5:
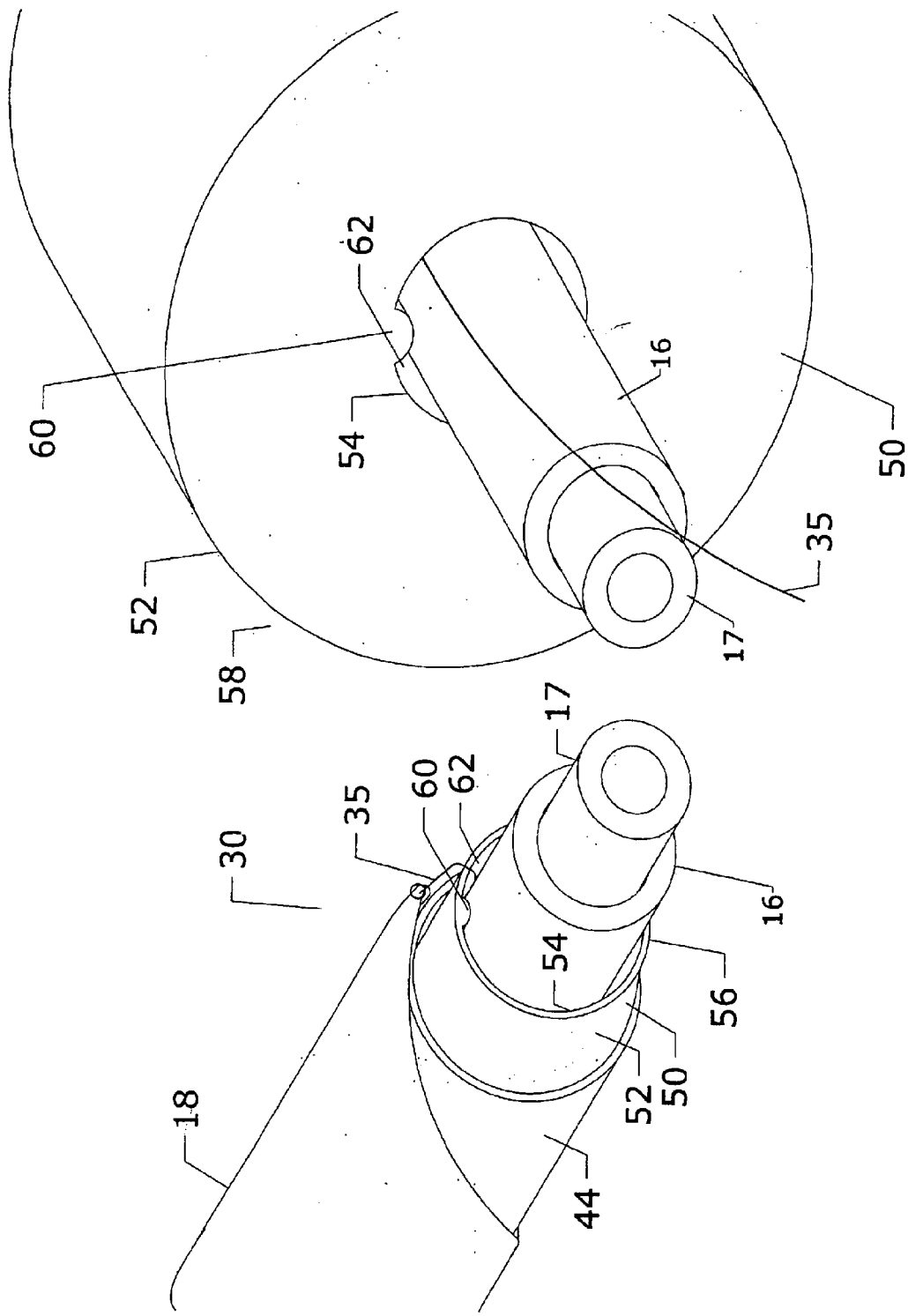
FIG. 5 illustrates a portion of an introducer element having a tubular spacer element.

In one embodiment of the invention a tubular spacer element 50 (see FIGS. 3–5) is provided for positioning on an introducer element, such as the introducer 10 adapted for catheterization depicted in FIG. 1. The tubular spacer element 50 is used to contain one or more of the retaining tethers 35 attached to the distal end 30 of the sheet 18. In this embodiment, the tubular spacer element 50 is disposed on the sheath 16 as depicted in FIG. 5. The positioning tube 44 is disposed on the tubular spacer element 50 and the sheet 18 is disposed on the positioning tube 44.

Figure 3A:
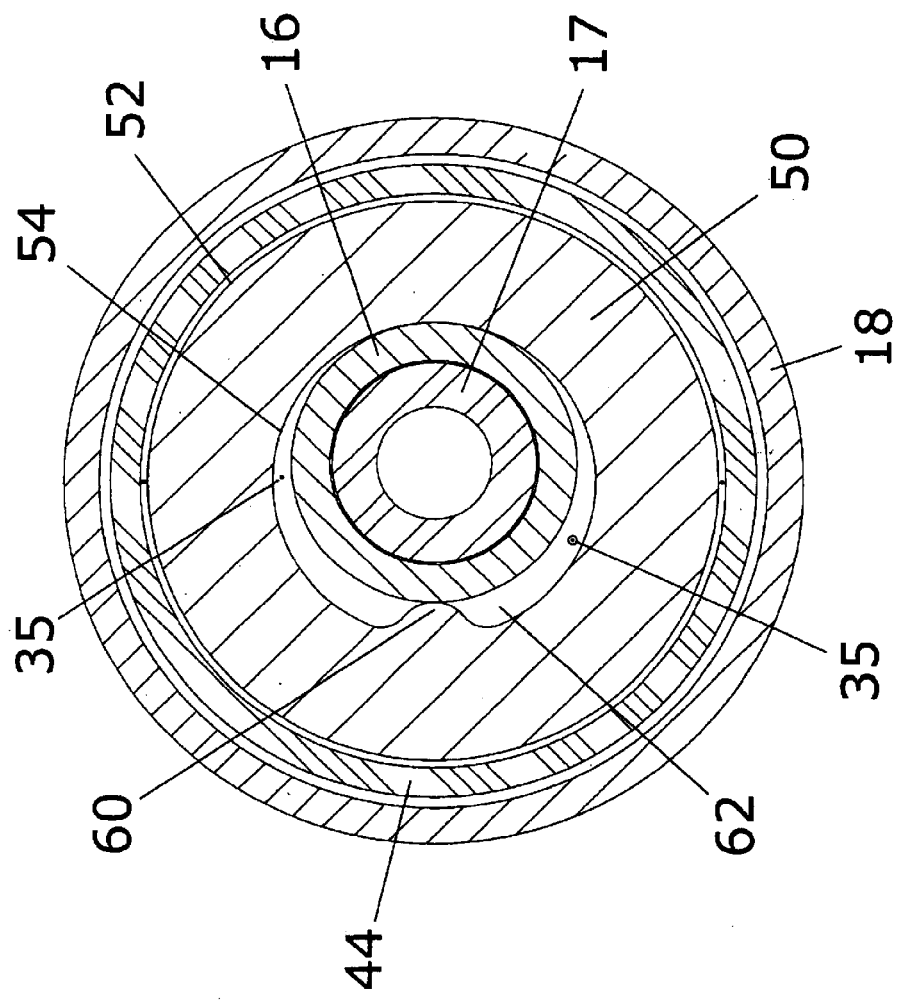
FIGS. 3 A–C illustrate views of various embodiments of a tubular spacer element.
Figure 3B:
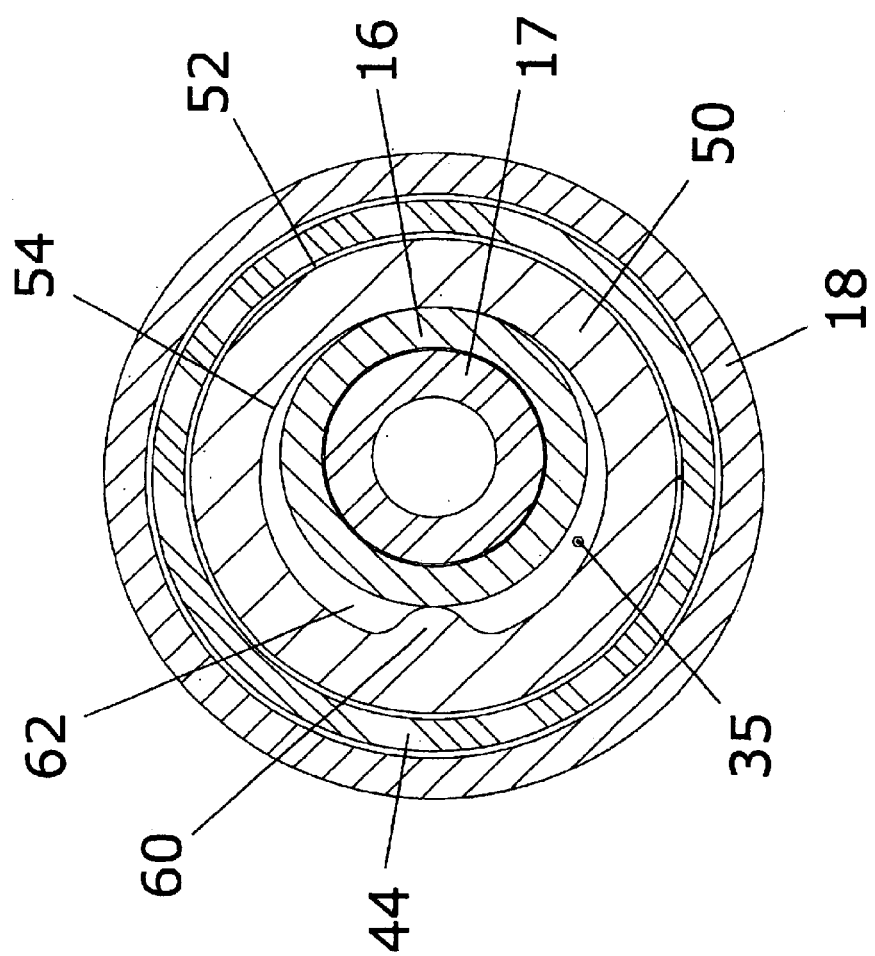

As shown in FIG. 5, the tubular spacer element 50 has an outer surface 52, an inner surface 54, a user distal end 56, a user proximal end 58, and at least one ridge 60 extending from the inner surface 54 of the spacer element 50. The distal end 56 of the spacer element 50 is inserted into the blood vessel and the proximal end 58 remains externally exposed. The ridge 60 prevents at least a portion of the inner surface 54 of the spacer element 50 from contacting the sheath 16 to provide at least one lumen 62 between the spacer element 50 and the sheath 16 for containing one or more tethers 35 attached to the distal end 30 (see FIG. 5) of the sheet 18. In another embodiment the tubular spacer element 50 has multiple ridges 60 providing multiple lumens 62 to contain one or more tethers 35. A plan view of one embodiment of the tubular spacer element 50 with a single ridge 60 is shown in FIGS. 3A–B and a plan view of the another embodiment with multiple ridges is shown in FIGS. 4A–B.

The tether 35 is inserted into the lumen 62 of the spacer element 50 at the distal end 56 of the spacer element 50 (see FIG. 5) between the tubular spacer element 50 and the sheath 16 and traverses the lumen 62 to the proximal end 58 of the spacer element 50. The proximal end 58 of the spacer element 50 is exposed externally when the introducer 10 is inserted into the tubular tissue structure. Thus, in one embodiment, the user can grasp the externally exposed portion of the tether 35 attached to the distal end 30 of the sheet 18 during insertion of the introducer 10 (i.e., the introducer having the spacer element 50 and the sheet 18) into a tubular tissue structure. As a result, the sheet 18 is prevented from rolling up the introducer 10 upon insertion into the blood vessel. In another embodiment the proximal end 51 of the retaining tether may be attached to the introducer 10, such as to the sheath cap 20 or to the valve cap 22, and the retaining tether 35 may be cut when the user desires to pull the sheet 18 into the puncture site using the pull-up tether 37.

The ridge 60 prevents the inner surface 54 of the spacer element 50 from contacting the sheath 16 to provide at least one lumen 62 between the spacer element and the sheath 16 for containing the tether 35. In accordance with the present invention more than one ridge 60 may be present on the inner surface 54 of the spacer element (see FIG. 4). In such a way, multiple lumens 62 are provided to contain multiple tethers 35 for use in preventing the sheet 18 from rolling up the introducer 10 upon insertion into the blood vessel. In another embodiment of the invention (see FIGS. 3C and 4C), the tubular spacer element 50 comprises a tube 66 with a lumen 62 to contain a tether 35 or multiple lumens 62 to contain multiple tethers 35 for preventing the sheet 18 from rolling up the introducer 10 upon insertion into the blood vessel. The tubular spacer element 50 may also be formed as a positioning tube if a tapered ledge is formed at the distal end 56 of the spacer element 50.

The invention also relates to an apparatus for containing a tether as shown in plan view in FIGS. 3A–B and FIGS. 4A–B. The apparatus comprises the tubular spacer element 50 for positioning on a sheath 16 wherein the tube has an inner surface 54, an outer surface 52, and at least one ridge 60 on the inner surface 54 to prevent the tubular spacer element 50 from contacting the sheath 16 to provide at least one lumen 62 for containing a tether 35. Embodiments comprising multiple ridges 60 as described above (FIGS. 4A–B) are also contemplated in accordance with the present invention. Alternatively, the ridges might be replaced with grooves in the tubular spacer element 50 to provide lumens 62 for containing tethers 35.

An apparatus comprising a tubular spacer element 50 comprising a tube 66 with one lumen 62 for containing a tether 35 as shown in plan view in FIG. 3C is also provided. Alternatively, this embodiment of the invention may comprise multiple lumens 62 to contain multiple tethers 35 as shown in FIG. 4C.

Any suitable means for preventing the sheet 18 from rolling up the introducer 10 upon insertion into a tubular tissue structure, such as a blood vessel, can be used. Other embodiments for preventing the sheet 18 from rolling up the introducer 10 are depicted in FIGS. 6–8.

Figure 6:
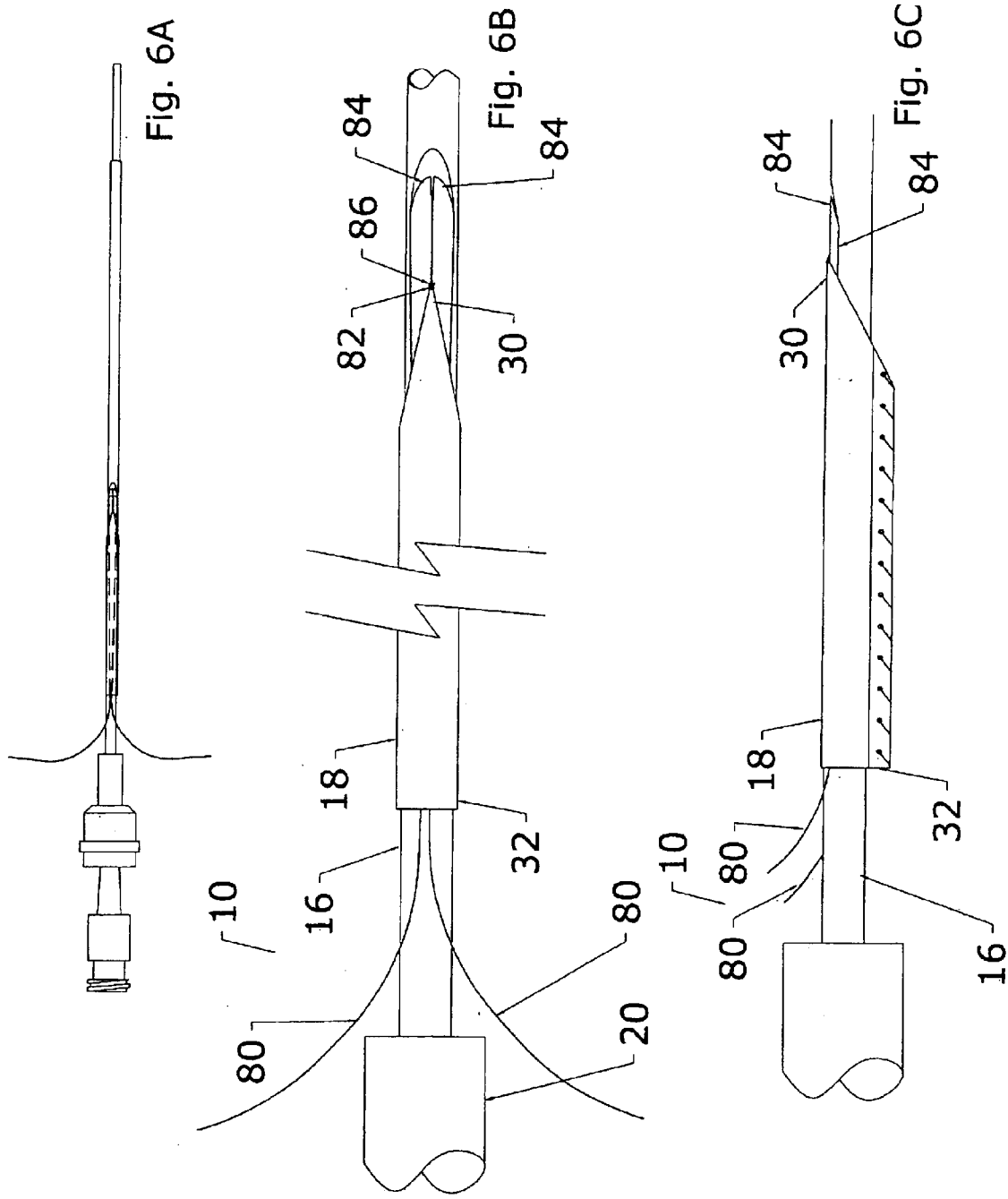
FIGS. 6A–6C illustrate an embodiment of a retaining mechanism.

As shown in FIG. 6, retaining tethers 80 may be used which are attached to the distal end 30 of the sheet 18 at an attachment point 82 on the distal end 30 of the sheet 18 and extend axially upwards between the sheet 18 and the positioning tube 44 towards the proximal end 14 of the introducer 10. The tethers 80 can be attached to the sheet 18, for example, by tying the tethers 80 to form a knot. Loops 86 are formed from the retaining tethers 80 and the loops 86 originate at the attachment point 82 (see FIG. 6A). The loops 86 can be fitted over flaps 84 cut in, or otherwise attached to the sheath 16, and the tethers 80 can be pulled towards the user proximal end 14 of the introducer 10 to tighten the loops 86 around the flaps 84 before the introducer 10 is inserted into the tubular tissue structure (see FIG. 6B).

Accordingly, the user can grasp the proximal end 32 of the sheet 18 and or the tethers 80 upon insertion of the introducer 10 into the tubular tissue structure and prevent the sheet 18 from rolling up the introducer 10. After insertion of the distal end 30 of the sheet 18 through the wall of the tubular tissue structure, the introducer 10 can be pulled towards the user enough to release the loops 86 from the flaps 84 cut in, or attached to, the sheath 16 to allow the distal end 30 of the sheet 18 to be gathered into the puncture site at the necessary time.

Figure 7:
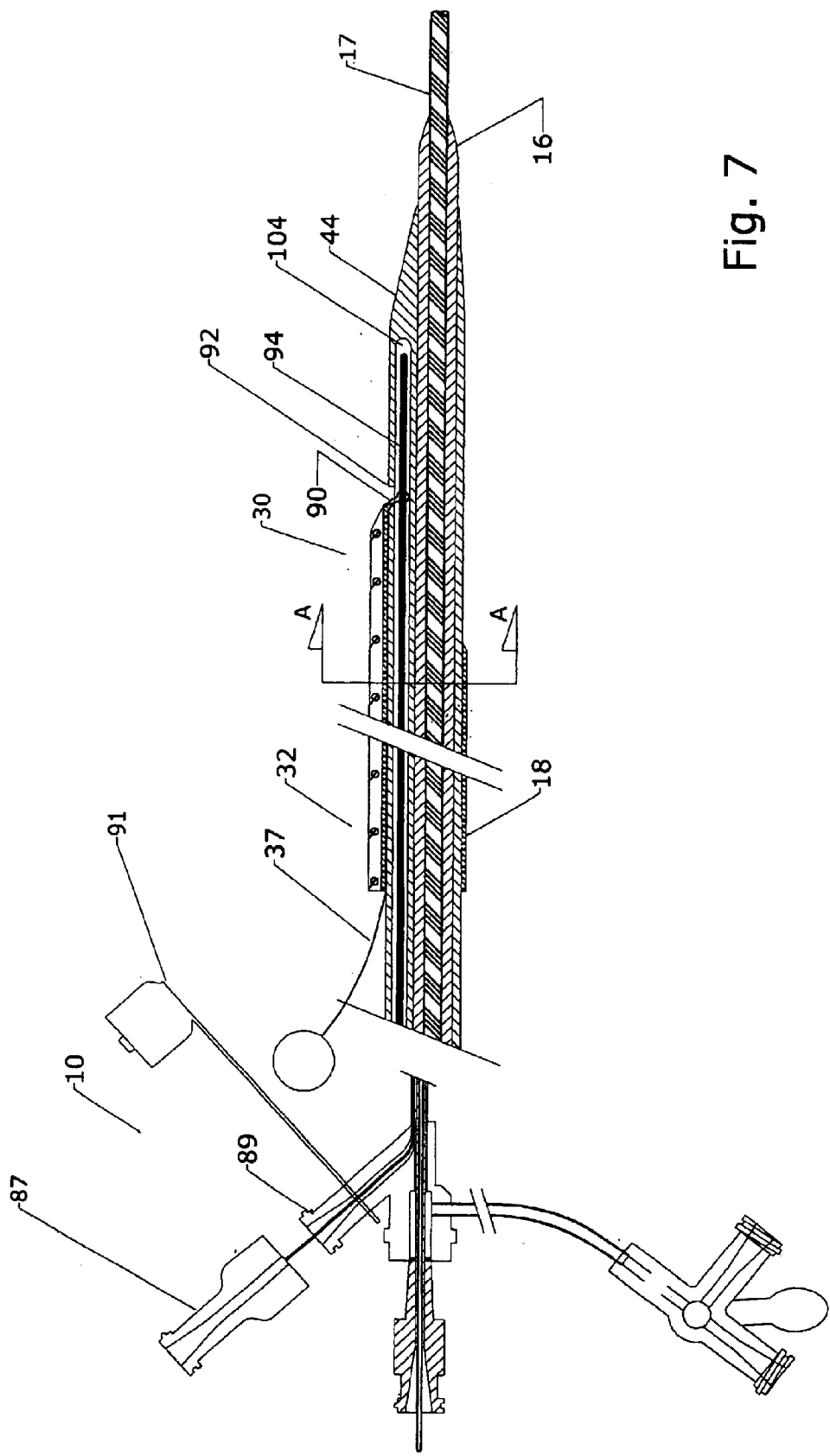
FIGS. 7, 7A and 7B illustrate an embodiment of a retaining mechanism.
Figure 7A:
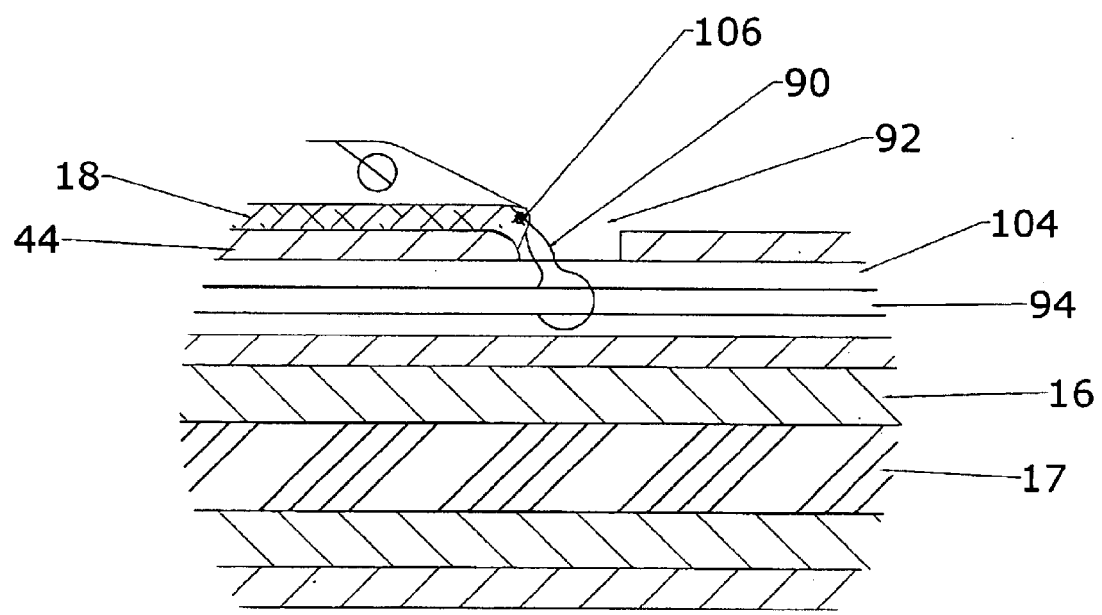
Figure 7B:
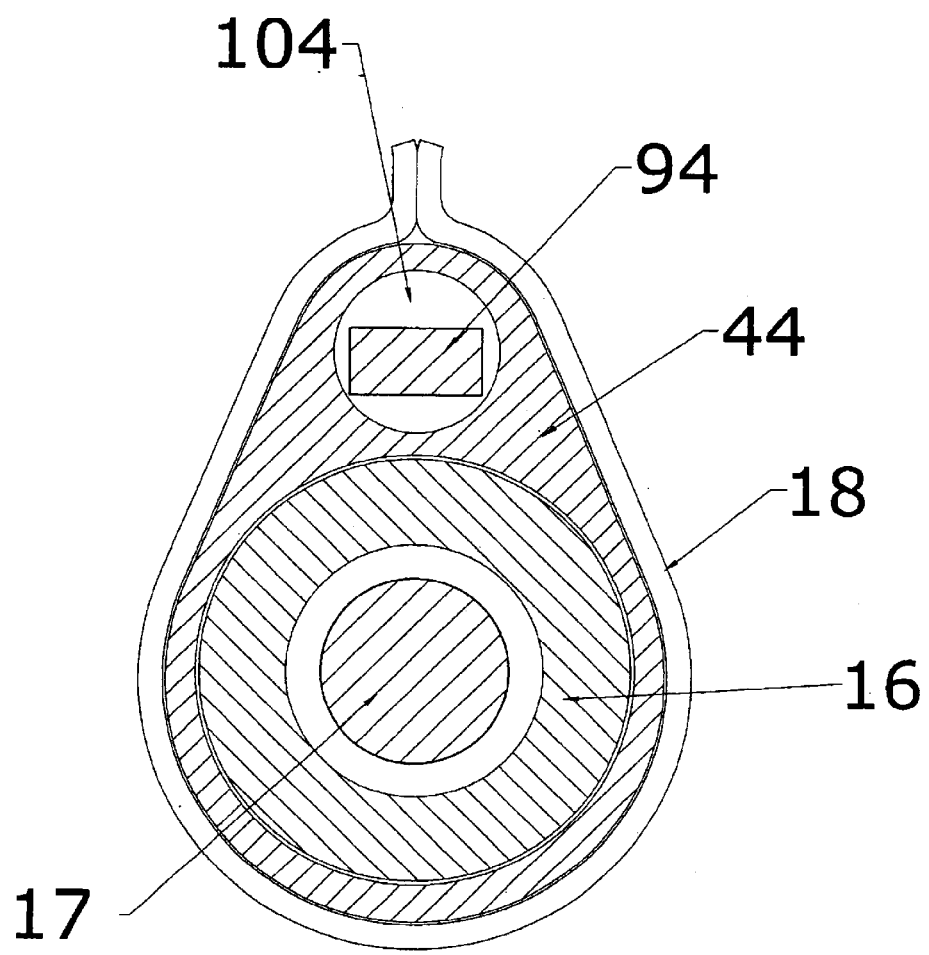
Figure 8A:
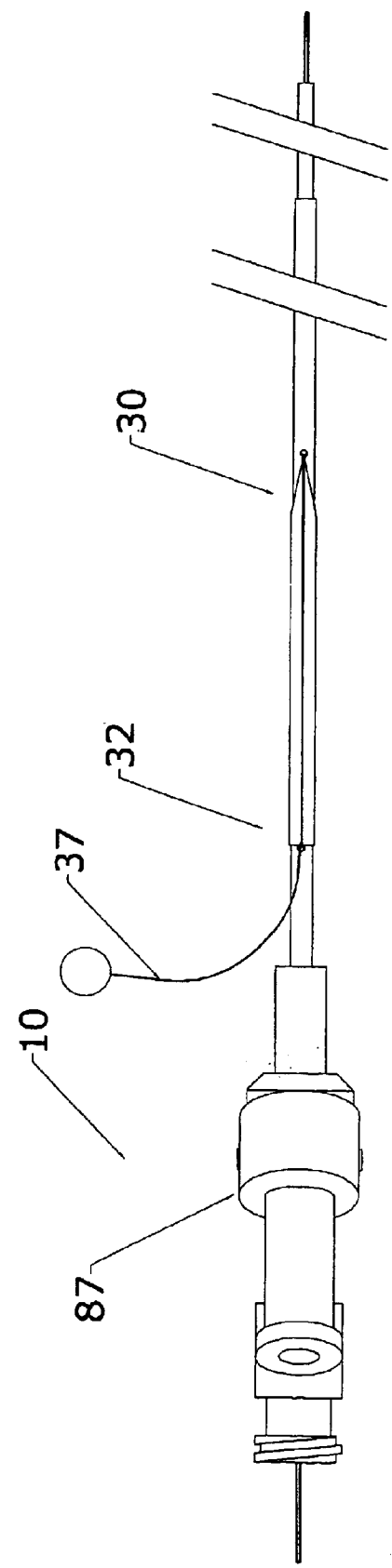
FIGS. 8 A–C illustrate an embodiment of a retaining mechanism and a mechanism for holding the sheet 18 in place on the introducer element.
Figure 8B:
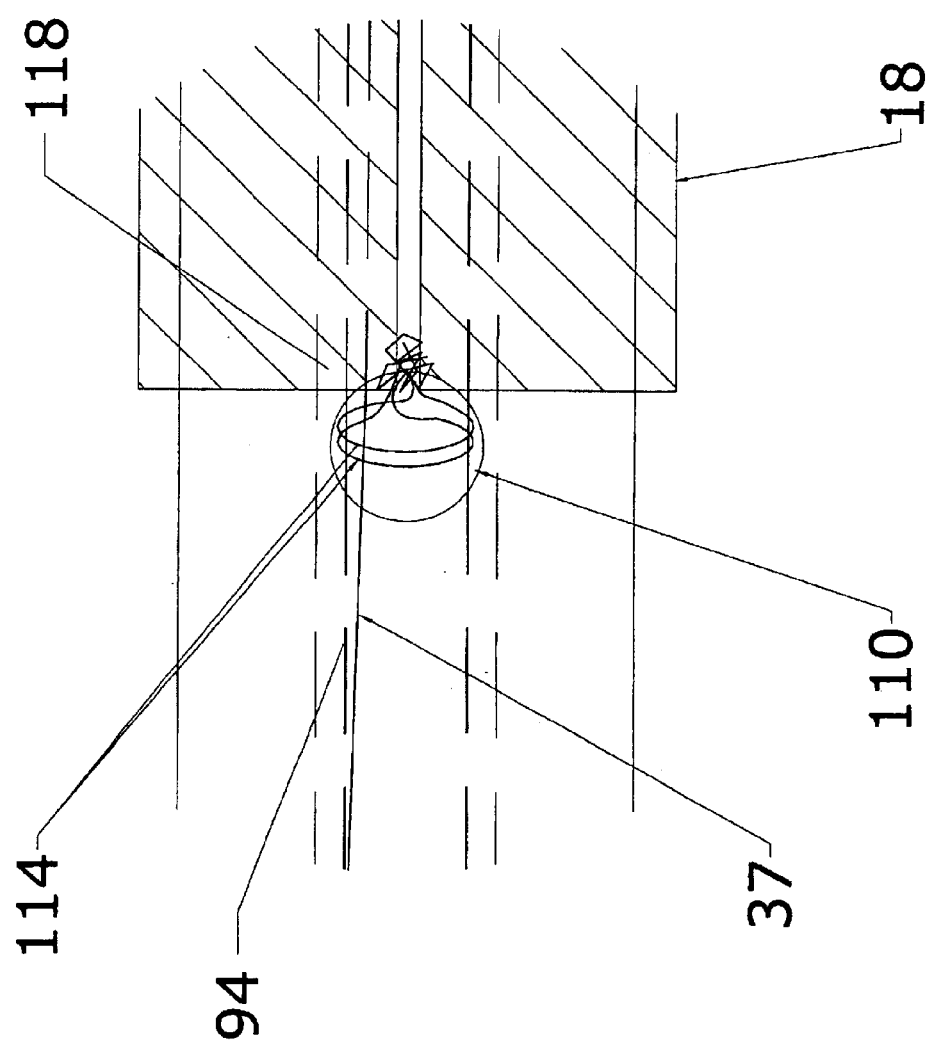
Figure 8C:
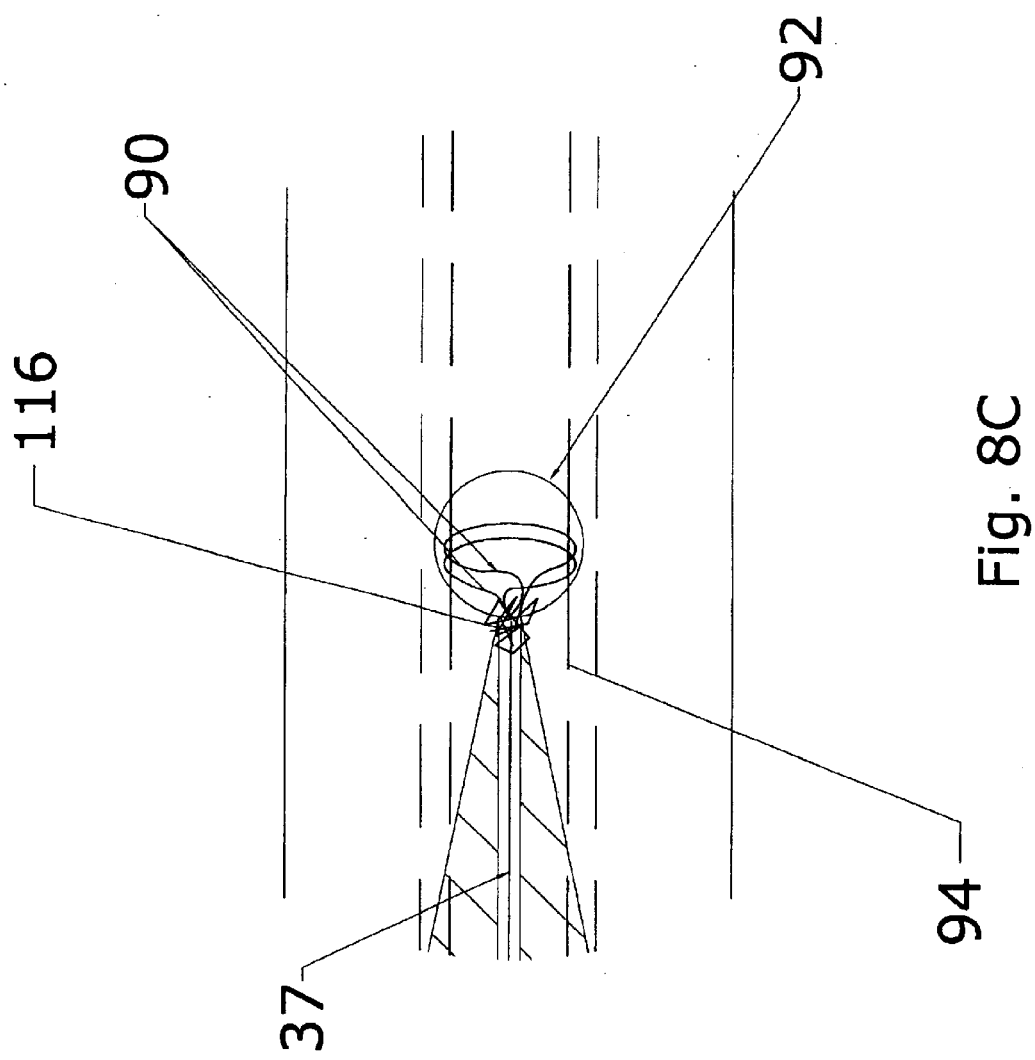
Figure 9A:
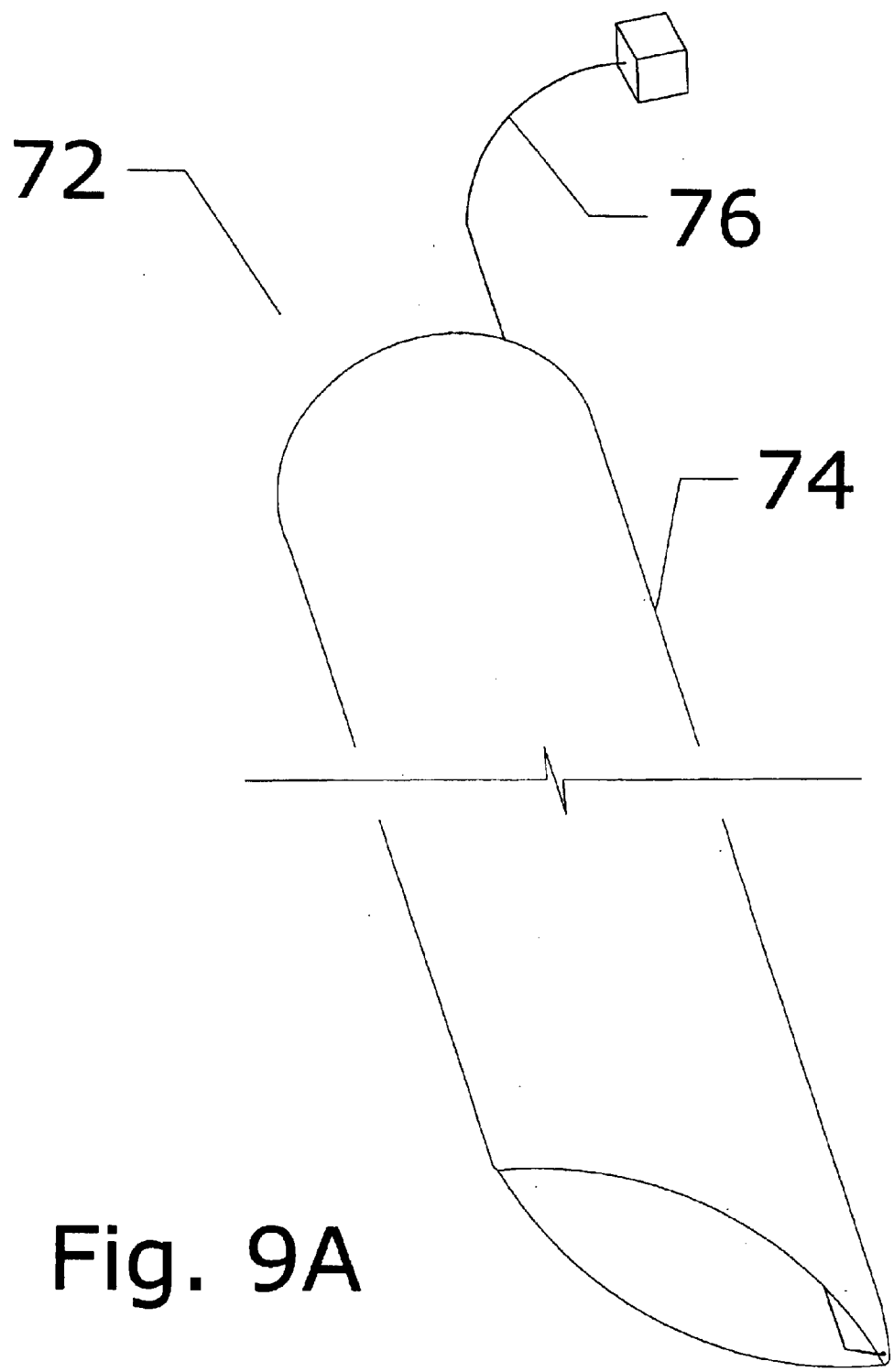
FIGS. 9 A and E, B and F, C and G, and D and H illustrate perspective views of the tops and bottoms, respectively, of various tissue graft embodiments.
Figure 9B:
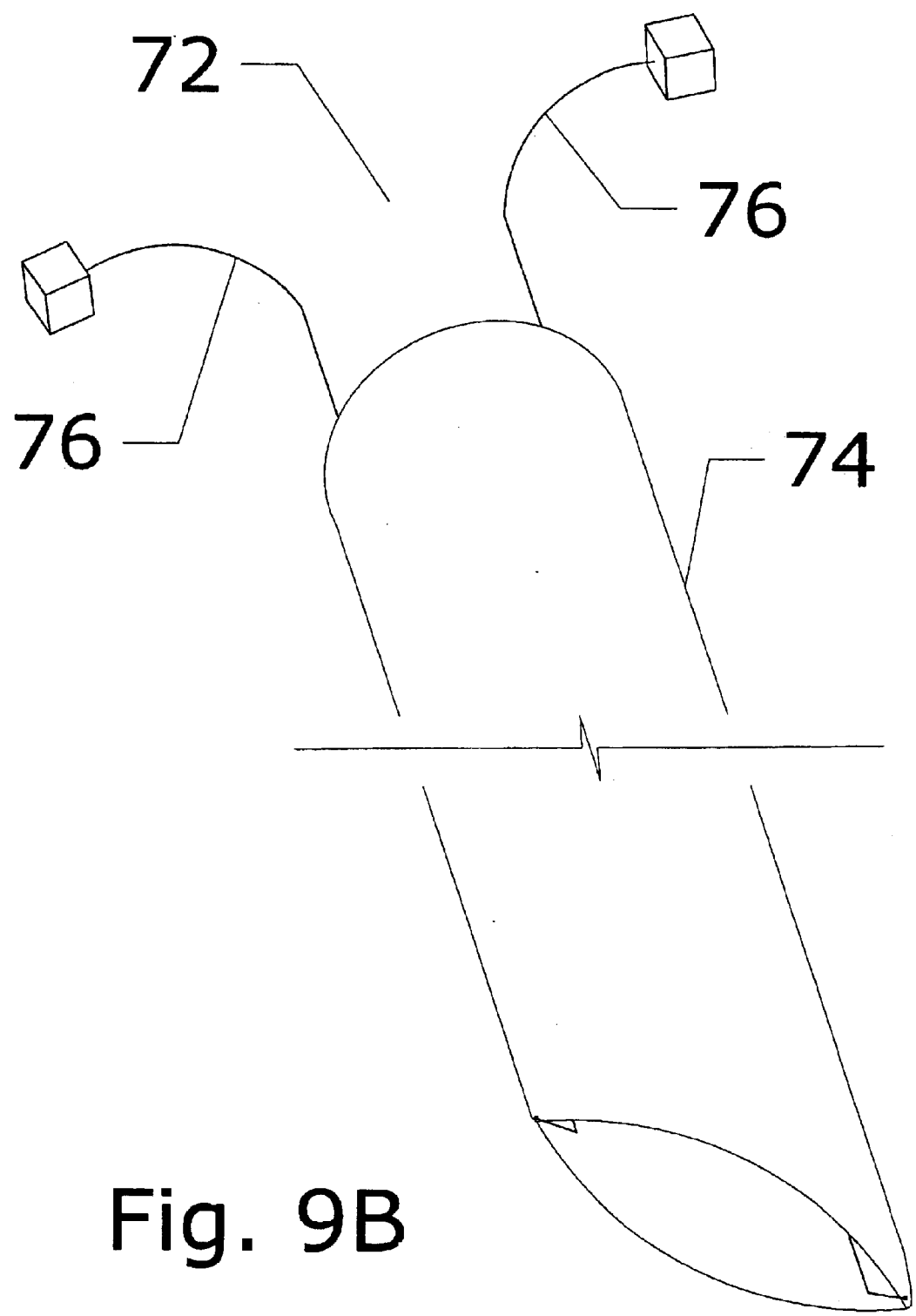
Figure 9C:
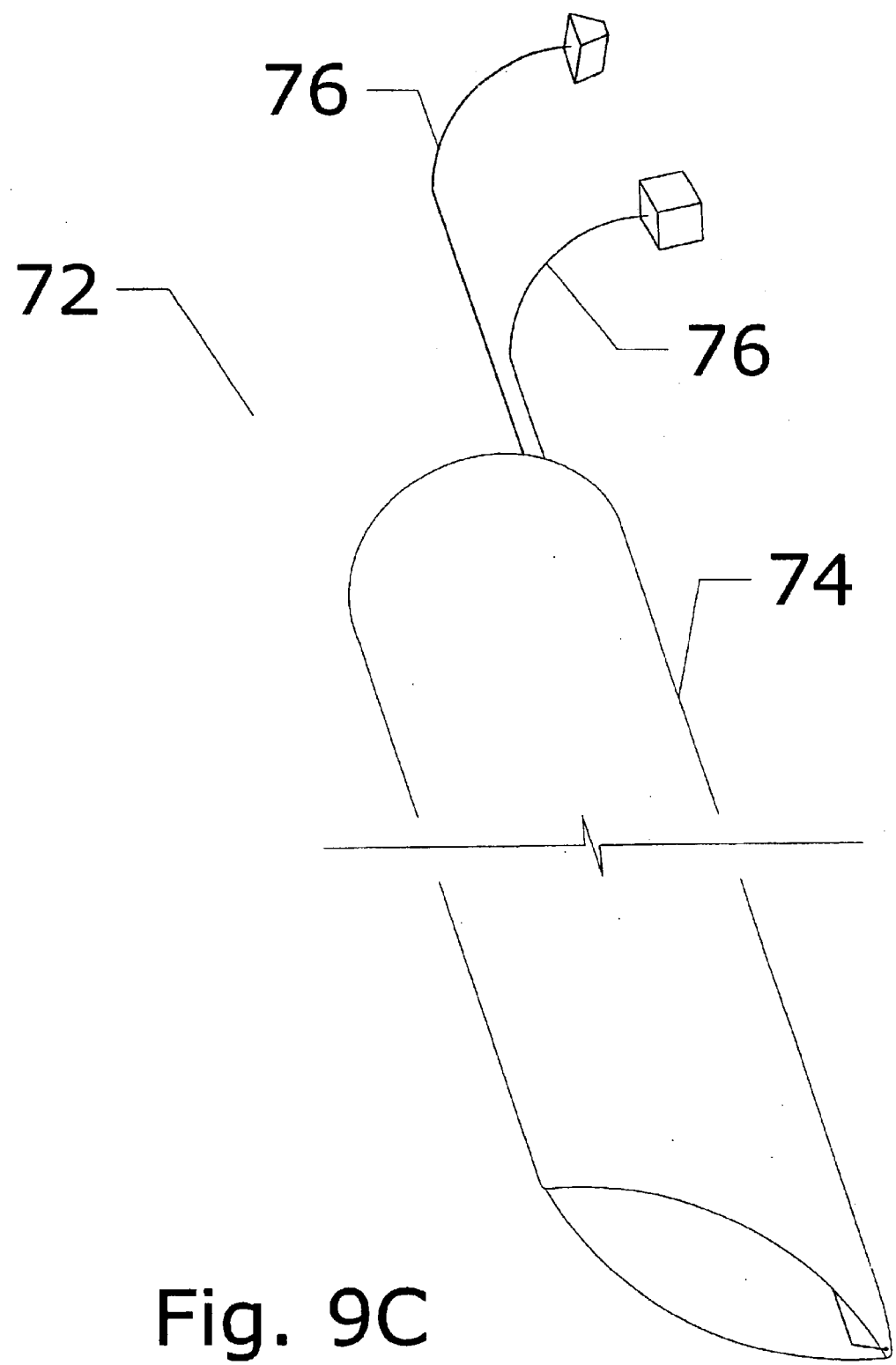
Figure 9D:
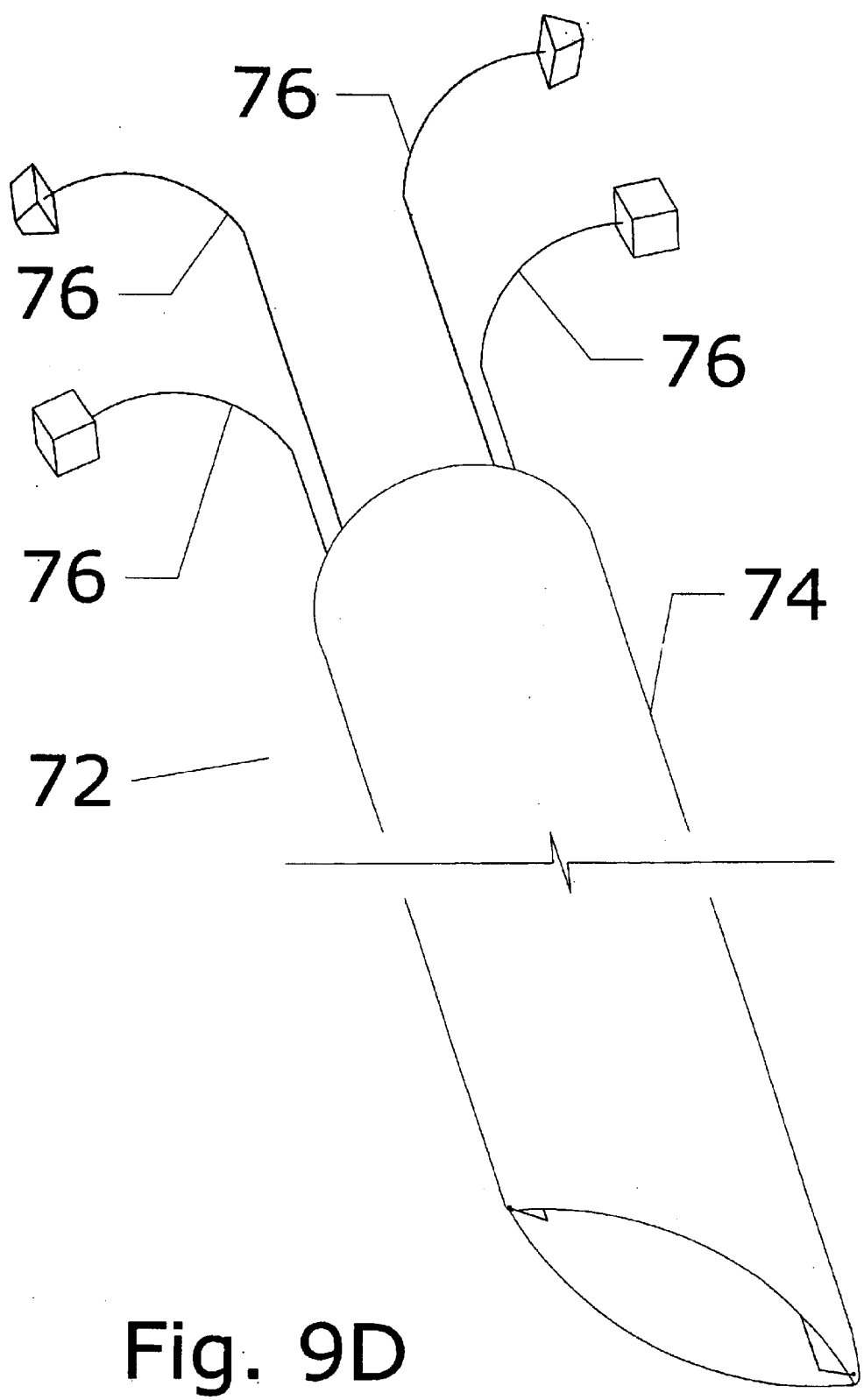
Figure 9E:
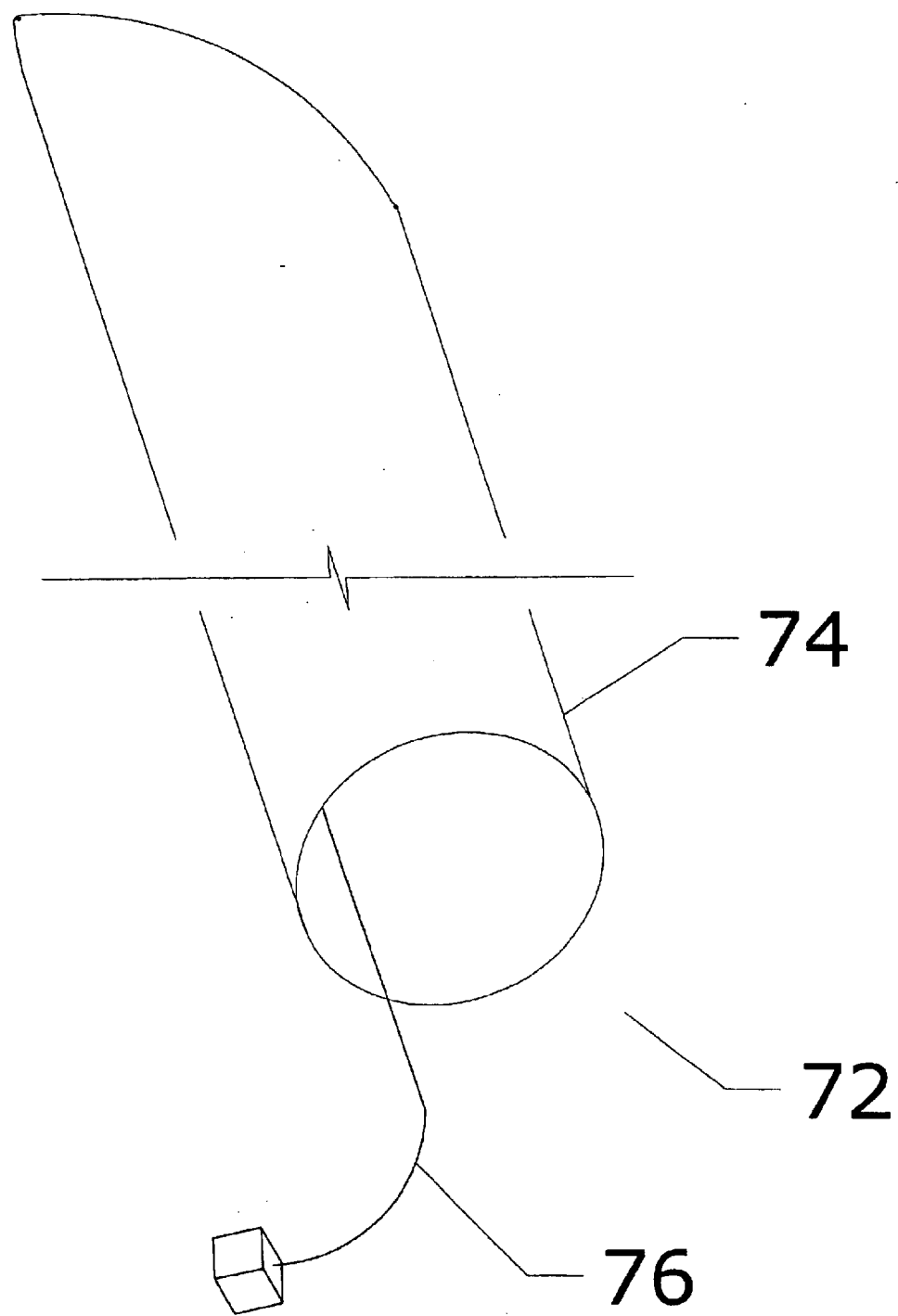
Figure 9F:
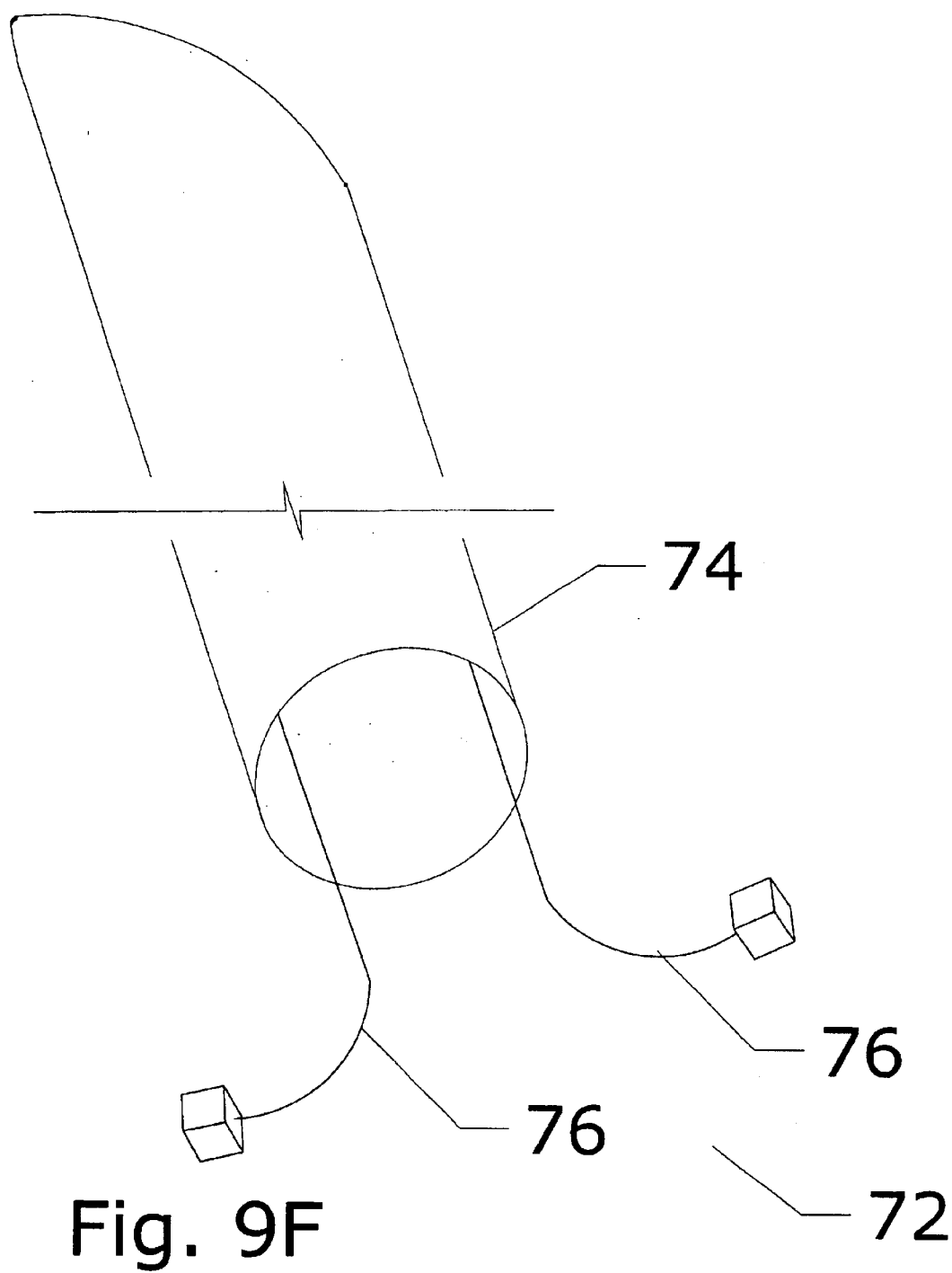
Figure 9G:
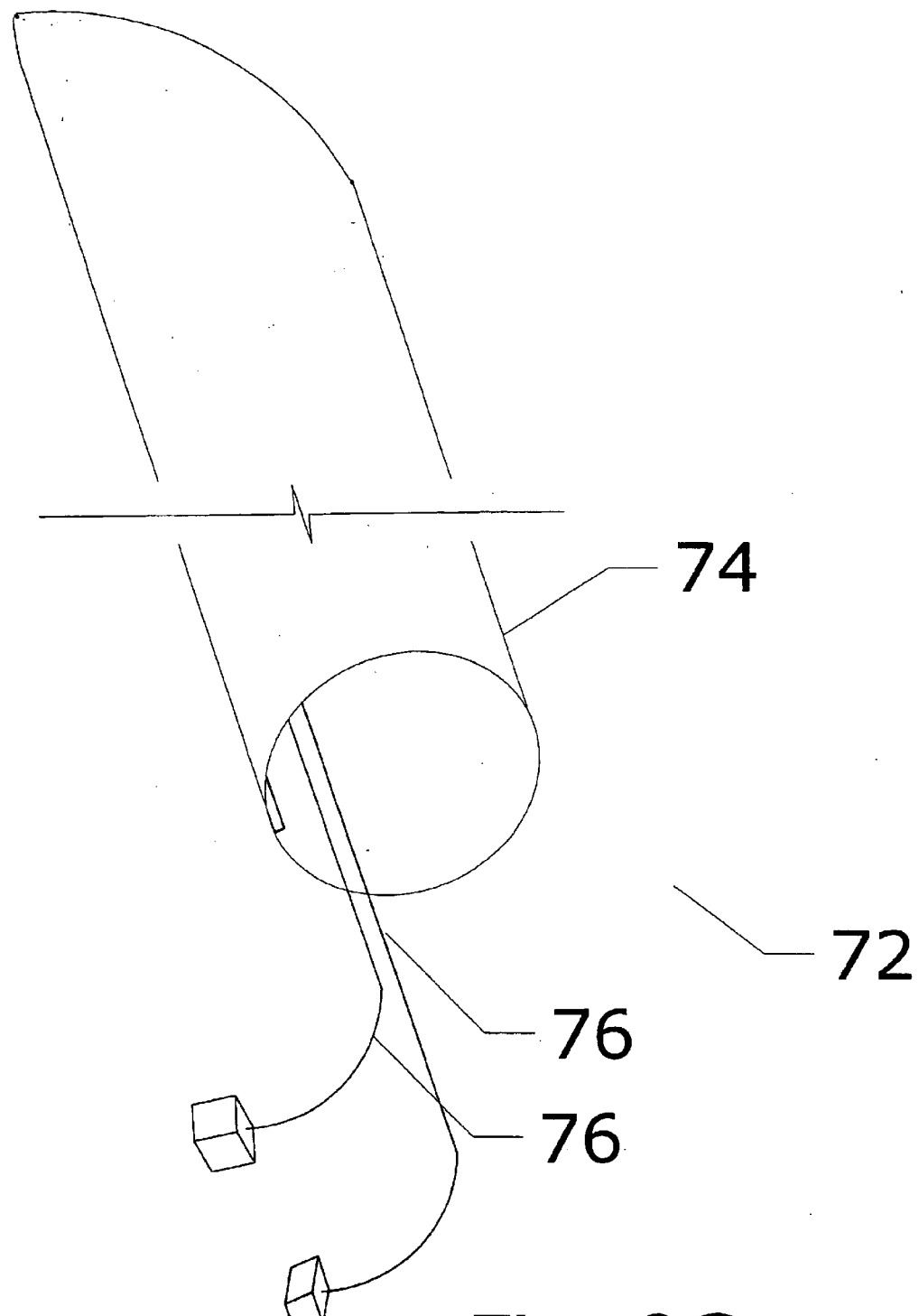
Figure 9H:
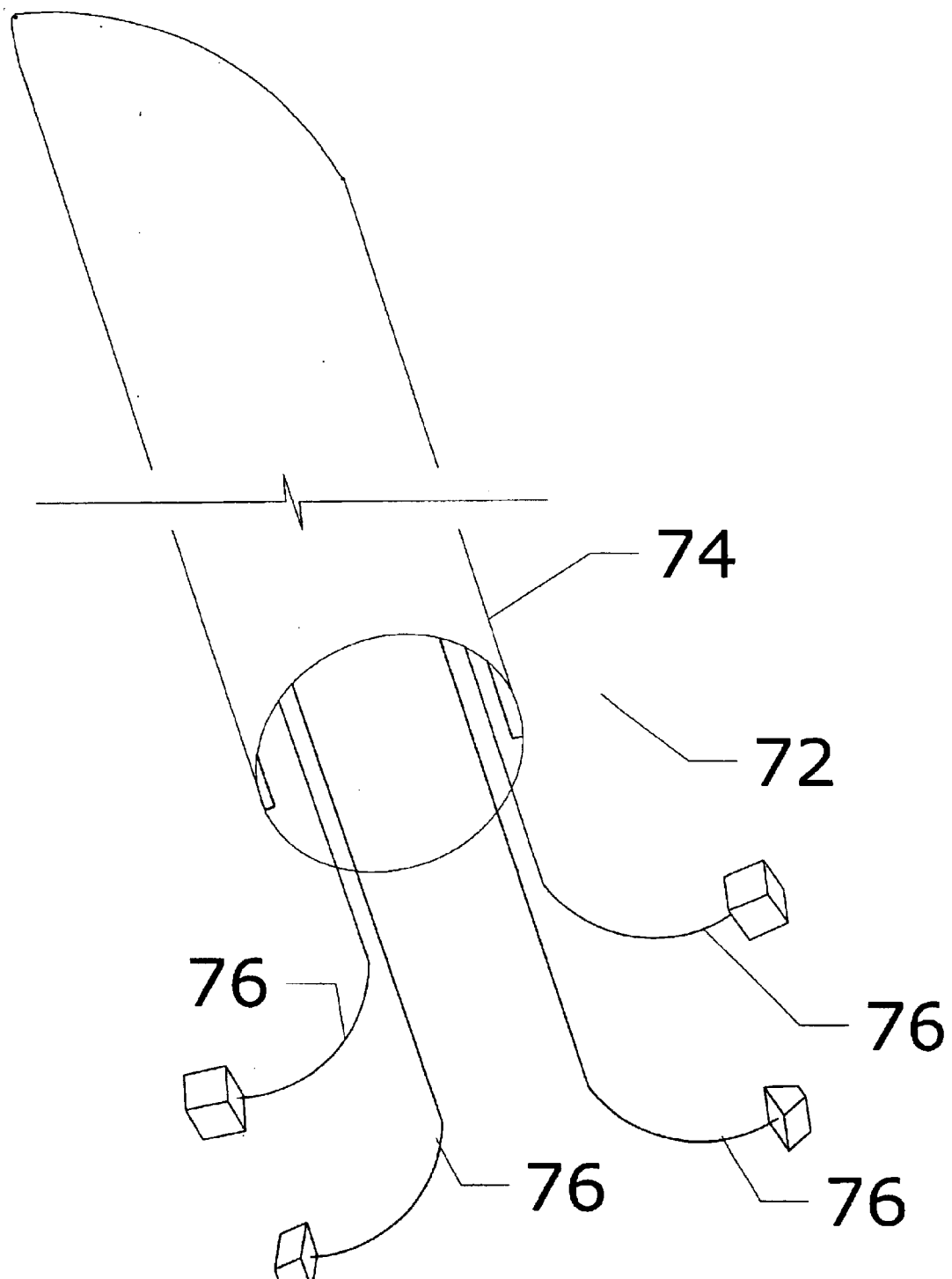

Another embodiment for preventing the sheet 18 from rolling up the sheath 16 upon insertion into a tubular tissue structure is shown in FIG. 7. In this embodiment, there is a lumen 104 in, for example, the positioning tube 44. A retaining wire 94 is attached to a cap 87 and the cap 87 is grasped by the user and is used to insert the retaining wire 94 into the lumen 104 through an insertion tube 89. The cap 87 can be screwed onto, or otherwise attached to, the introducer 10 to hold the retaining wire 94 in place in the lumen 104.

As the retaining wire 94 is inserted into the lumen 104, the retaining wire 94 is threaded through a tether 90, in the form of a loop attached to the distal end 30 of the sheet 18 at an attachment point 106. The tether 90 can be attached to the sheet 18, for example, by tying the tether 90 to form a knot. The tether 90 extends radially inwards into the lumen 104 through an access port 92.

Accordingly, the tether 90, anchored by the retaining wire 94, will prevent the sheet 18 from rolling up the introducer 10 upon insertion into the tubular tissue structure. After insertion of the introducer 10 with the sheet 18 through the wall of the tubular tissue structure, the retaining wire 94 can be removed from the lumen 104 by releasing the cap 87 from the introducer 10 and by pulling the retaining wire 94, attached to the cap 87, out of the lumen 104. Thus, the tether 90 is no longer anchored by the retaining wire 94. A replacement cap 91 can be used to close the insertion tube 89. After completion of the procedure (e.g., a catheterization procedure), the pull-up tether 37 can be used to gather the distal end 30 of the sheet 18 into the puncture site.

FIG. 8 shows an embodiment similar to the embodiment depicted in FIG. 7 except that both the proximal end 32 and the distal end 30 of the sheet 18 are held in place by tethers 90 and 114, in the form of loops, attached to the distal end 30 and the proximal end 32 of the sheet 18, respectively. The tethers 90 and 114 are attached to the sheet 18 at attachment points 116 and 118, respectively. The retaining wire 94 is threaded through the tethers 90 and 114. The tether 114 attached to the proximal end 32 of the sheet 18 is used to hold the proximal end 32 of the sheet 18 in place, particularly when the sheet 18 is in the form of a ribbon with edges that are not joined by, for example, suturing (ribbon forms of the sheet 18 are described below).

As shown in FIG. 9, a tissue graft 72 for sealing a puncture site in the wall of a tubular tissue structure, such as a blood vessel, is also provided in accordance with the present invention. The tissue graft 72 comprises a sheet 74 of submucosal tissue or another extracellular matrix-derived tissue and at least one tether 76 attached at or near at least one end of the sheet 74. The sheet 74 can be in any of the forms described below (i.e., a tube, a disk, a roll, a ribbon, or the like). In alternate embodiments of the invention one tether may be attached near one end of the sheet 74 (see FIG. 9A), more than one tether may be attached near one end of the sheet 74 (see FIG. 9B), one tether may be attached near each end of the sheet 74 (see FIG. 9C), or more than one tether may be attached at both ends of the sheet 74 (see FIG. 9D). The tethers can be in the form of loops.

The submucosal tissue or another extracellular matrix-derived tissue can be in the form of a ribbon with unjoined edges (see FIG. 8), a cylindrically-shaped tube with joined edges (see FIG. 6, view B), a disk, a roll wrapped multiple times around the introducer 10, or in any other form suitable for use in accordance with the invention.

Exemplary of tissues that can be used to make the sheet 18 are submucosal tissues or any other extracellular matrix-derived tissue of a warm-blooded vertebrate. Submucosal tissue can comprise submucosal tissue selected from the group consisting of intestinal submucosa, stomach submucosa, urinary bladder submucosa, and any other submucosal tissue that is acellular and can be used to remodel endogenous tissue. The submucosal tissue can comprise the tunica submucosa delaminated from both the tunica muscularis and at least the luminal portion of the tunica mucosa of a warm-blooded vertebrate.

It is known that compositions comprising the tunica submucosa delaminated from both the tunica muscularis and at least the luminal portion of the tunica mucosa of the submucosal tissue of warm-blooded vertebrates can be used as tissue graft materials (see, for example, U.S. Pat. Nos. 4,902,508 and 5,281,422 incorporated herein by reference). Such submucosal tissue preparations are characterized by excellent mechanical properties, including high compliance, high tensile strength, a high burst pressure point, and tear-resistance. Thus, the sheets 18 prepared from submucosal tissue are tear-resistant preventing occlusive material from being disposed into the blood vessel.

Other advantages of the submucosal tissue sheets are their resistance to infection, stability, and lack of immunogenicity. Intestinal submucosal tissue, fully described in the aforesaid patents, has high infection resistance. In fact, most of the studies done with intestinal submucosa grafts to date have involved non-sterile grafts, and no infection problems have been encountered. Of course, appropriate sterilization techniques can be used to treat submucosal tissue. Furthermore, this tissue is not recognized by the host's immune system as "foreign" and is not rejected. It has been found that xenogeneic intestinal submucosa is not rejected following implantation as vascular grafts, ligaments, and tendons because of its composition (i.e., submucosal tissue is apparently similar among species). It has also been found that submucosal tissue has a long shelf-life and remains in good condition for at least two months at room temperature without any resultant loss in performance.

Submucosa-derived matrices are collagen based biodegradable matrices comprising highly conserved collagens, glycoproteins, proteoglycans, and glycosaminoglycans in their natural configuration and natural concentration. Such submucosal tissue used as a sheet 18 on an introducer element serves as a matrix for the regrowth of endogenous connective tissues at the puncture site (i.e., biological remodeling begins to occur upon insertion of the introducer element with the submucosal tissue sheet 18 into the blood vessel). The submucosal tissue sheet 18 serves as a rapidly vascularized matrix for support and growth of new endogenous connective tissue. Thus, submucosal tissue has been found to be trophic for host tissues with which it is attached or otherwise associated in its implanted environment. In multiple experiments submucosal tissue has been found to be remodeled (resorbed and replaced with autogenous differentiated tissue) to assume the characterizing features of the tissue(s) with which it is associated at the site of implantation or insertion. Additionally, the boundaries between the submucosal tissue and endogenous tissue are not discernible after remodeling. Thus, it is an object of the present invention to provide submucosal tissue for use as a connective tissue substitute, particularly to remodel a puncture site in the wall of a tubular tissue structure or the wall of a body cavity to form a hemostatic seal at the puncture site.

Small intestinal tissue is a preferred source of submucosal tissue for use in this invention. Submucosal tissue can be obtained from various sources, for example, intestinal tissue can be harvested from animals raised for meat production, including, pigs, cattle and sheep or other warm-blooded vertebrates. Small intestinal submucosal tissue is a plentiful by-product of commercial meat production operations and is, thus, a low cost material.

Suitable intestinal submucosal tissue typically comprises the tunica submucosa delaminated from both the tunica muscularis and at least the luminal portion of the tunica mucosa. In one embodiment the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of submucosal tissue is described in U.S. Pat. No. 4,902,508, the disclosure of which is expressly incorporated herein by reference. A segment of vertebrate intestine, for example, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed with saline and is optionally sterilized.

The submucosal tissue for use as a sheet 18 on an introducer element can be sterilized using conventional sterilization techniques including glutaraldehyde tanning, formaldehyde tanning at acidic pH, propylene oxide or ethylene oxide treatment, gas plasma sterilization, gamma radiation, electron beam, peracetic acid sterilization. Sterilization techniques which do not adversely affect the mechanical strength, structure, and biotropic properties of the submucosal tissue are preferred. For instance, strong gamma radiation may cause loss of strength of the sheets of submucosal tissue. Preferred sterilization techniques include exposing the submucosal tissue sheet to peracetic acid, 1–4 Mrads gamma irradiation (more preferably 1–2.5 Mrads of gamma irradiation), ethylene oxide treatment or gas plasma sterilization. Peracetic acid sterilization is the most preferred sterilization method.

Typically, the submucosal tissue is subjected to two or more sterilization processes. After the submucosal tissue is sterilized, for example, by chemical treatment, the tissue can be wrapped in a plastic or foil wrap, for example, as packaging for the preparation, and sterilized again using electron beam or gamma irradiation sterilization techniques. Alternatively, the introducer element can be assembled with the submucosal tissue sheet 18 on the introducer element and the complete assembly can be packaged and sterilized a second time.

The submucosal tissue can be stored in a hydrated or dehydrated state. Lyophilized or air dried submucosa tissue can be rehydrated and used without significant loss of its biotropic and mechanical properties. The submucosal tissue can be rehydrated before use or, alternatively, is rehydrated during use upon insertion through the skin and into the tubular tissue structure, such as a blood vessel, or a body cavity.

The submucosal tissue can be conditioned, as described in U.S. Pat. No. 5,275,826 (the disclosure of which is expressly incorporated herein by reference) to alter the viscoelastic properties of the submucosal tissue. In accordance with one embodiment submucosa tissue delaminated from the tunica muscularis and luminal portion of the tunica mucosa is conditioned to have a strain of no more than 20%. The submucosal tissue is conditioned by stretching, chemically treating, enzymatically treating or exposing the tissue to other environmental factors. In one embodiment the submucosal tissue is conditioned by stretching in a longitudinal or lateral direction so that the submucosal tissue has a strain of no more than 20%.

When a segment of intestine is first harvested and delaminated as described above, it will be a tubular segment having an intermediate portion and opposite end portions. To form the submucosal tissue sheets 18, sheets of delaminated submucosal tissue can be cut from this tubular segment of intestine to form squares or rectangles of the desired dimensions. The edges of the squares or rectangles can be overlapped and can be joined to form a tubular structure or the edges can be left unjoined. In embodiments where the edges are left unjoined, the sheet 18 can be held in place on the sheath 16, for example, as depicted in FIG. 8 (described above). Thus, the sheet 18 can be in the form of a ribbon with unjoined edges, a tubular structure with overlapped, joined edges, a roll of tissue wrapped around the sheath 16 multiple times, a disk, as described above, or in any other form suitable for use in accordance with the present invention. Such embodiments of the sheet 18 are applicable to submucosal tissue or to other extracellular matrix-derived tissues, and to use with any type of introducer element.

In one embodiment, the edges of the prepared squares or rectangles can be overlapped and joined to form a cylinder-shaped submucosal tissue sheet 18 with the desired diameter. The edges can be joined and a cylinder-shaped sheet formed by applying pressure to the sheet 18 including the overlapped portions by compressing the submucosal tissue between two surfaces. The two surfaces can be formed from a variety of materials and in any cylindrical shape depending on the desired form and specification of the sheet 18. Typically, the two surfaces used for compression are formed as a cylinder and a complementary nonplanar curved plate. Each of these surfaces can optionally be heated or perforated. In preferred embodiments at least one of the two surfaces is water permeable. The term water permeable surface as used herein includes surfaces that are water absorbent, microporous or macroporous. Macroporous materials include perforated plates or meshes made of plastic, metal, ceramics or wood.

The submucosal tissue is compressed in accordance with one embodiment by placing the sheet 18 including the overlapped portions of the sheets of submucosal tissue on a first surface (i.e., inserting a cylinder of the desired dimensions in a cylinder of submucosal tissue) and placing a second surface on top of the exposed submucosal surface. A force is then applied to bias the two surfaces (i.e., the plates) towards one another, compressing the submucosal tissue between the two surfaces. The biasing force can be generated by any number of methods known to those skilled in the art including the application of a weight on the top plate, and the use of a hydraulic press or the application of atmospheric pressure on the two surfaces.

In one preferred embodiment the strips of submucosal tissue are subjected to conditions allowing dehydration of the submucosal tissue concurrent with the compression of the tissue. The term "conditions allowing dehydration of the submucosal tissue" is defined to include any mechanical or environmental condition which promotes or induces the removal of water from the submucosal tissue at least at the points of overlap. To promote dehydration of the compressed submucosal tissue, at least one of the two surfaces compressing the tissue can be water permeable. Dehydration of the tissue can optionally be further enhanced by applying blotting material, heating the tissue or blowing air across the exterior of the two compressing surfaces.

The submucosal tissue is typically compressed for 12–48 hours at room temperature, although heat may also be applied. For example, a warming blanket can be applied to the exterior of the compressing surfaces to raise the temperature of the compressed tissue up to about 50° C. to about 400° C. The overlapped portions are usually compressed for a length of time determined by the degree of dehydration of the tissue. The use of heat increases the rate of dehydration and thus decreases the amount of time the submucosal tissue is required to be compressed. Sufficient dehydration of the tissue is indicated by an increase in impedance of electrical current flowing through the tissue. When impedance has increased by 100–200 ohms, the tissue is sufficiently dehydrated and the pressure can be released.

A vacuum can optionally be applied to submucosal tissue during the compression procedure. The applied vacuum enhances the dehydration of the tissue and may assist the compression of the tissue. Alternatively, the application of a vacuum can provide the sole compressing force for compressing the submucosal tissue including the overlapped edges. For example, the submucosal tissue can be placed between two surfaces, preferably one of which is water permeable. The apparatus is covered with blotting material, to soak up water, and a breather blanket to allow air flow. The apparatus is then placed in a vacuum chamber and a vacuum is applied, generally ranging from 14–70 inches of Hg (7–35 psi). Preferably a vacuum is applied at approximately 51 inches of Hg (25 psi). Optionally a heating blanket can be placed on top of the chamber to heat the submucosal tissue during the compression of the tissue. Chambers suitable for use in this embodiment are known to those skilled in the art and include any device that is equipped with a vacuum port. The resulting drop in atmospheric pressure coacts with the two surfaces to compress the submucosal tissue and simultaneously dehydrate the submucosal tissue. The compressed submucosal tissue can be removed from the two surfaces as a cylinder. The construct can be further manipulated (i.e., tethers can be attached) as described above.

In alternate embodiments, the overlapped portions of the submucosal tissue sheet can be attached to each other by suturing with resorbable thread or by any other method of bonding the overlapped edges known to a person skilled in the art. Such methods of attaching the overlapped edges of the sheet to each other can be used with or without compression to form, for example, a cylindrically-shaped tube, a roll, or a disk. The sheet 18 can also be formed from multiple layers of submucosal tissue attached to each by compression as described above. The diameter of the sheet 18 can vary depending on the desired specifications of the sheet. For example, the diameter of the sheet can be from about 3 to about 12 french when a sheet 18 is used on an introducer element adapted for catheterization but any diameter can be used depending on the diameter of the introducer element.

Methods of preparing other extracellular matrix-derived tissues are known to those skilled in the art and may be similar to those described above for submucosal tissue. For example, see WO 01/45765 and U.S. Pat. No. 5,163,955, incorporated herein by reference. Extracellular matrix-derived tissues include such tissue preparations as liver basement membrane, pericardial tissue preparations, sheet-like collagen preparations, and the like. Any of these preparations, or the submucosal tissue preparations described above, can be impregnated with biological response modifiers such as glycoproteins, glycosaminoglycans, chondroitin compounds, laminin, thrombin and other clotting agents, growth factors, and the like, or combinations thereof.

The present invention is also directed to a method of sealing a puncture site in the wall of a tubular tissue structure or the wall of a body cavity. The method comprises the step of inserting submucosal tissue or another intact extracellular matrix-derived tissue of a warm-blooded vertebrate into the puncture site. In accordance with the invention, "intact extracellular matrix-derived tissue" means an extracellular matrix-derived tissue at least a portion of which is in its native three-dimensional configuration. The tissue can be in the form of, for example, a ribbon, a cylindrically-shaped tube, a disk, or a roll and can be inserted into the puncture site in the form of a sheet 18 on any type of introducer element used to provide access to the lumen of a tubular tissue structure or to access a body cavity.

In one embodiment the method comprises the step of inserting an introducer element into the puncture site. An exemplary embodiment is depicted in FIG. 10A and the introducer 10 has a sheet 18 comprising submucosal tissue or another extracellular matrix-derived tissue of a warm-blooded vertebrate and the sheet 18 has a user distal end 30 and a user proximal end 32. The user proximal end 32 of the sheet 18 remains outside of the punctured wall and the user distal end 30 of the sheet 18 is inserted into the tubular tissue structure 78. The sheet 18 has at least one tether 37 for positioning the user distal end 30 relative to the puncture site. The method further comprises the steps of pulling the tether 37 to position the user distal end 30 of the sheet 18 relative to the puncture site (see FIG. 10C) and further pulling the tether 37 to position the user distal end 30 of the sheet 18 within the puncture site (see FIG. 10D) to seal the puncture site upon removal of the introducer 10 from the tubular tissue structure 78 (see FIGS. 10E–F).

As is illustrated in FIGS. 10A–F, in one embodiment of the invention a puncture site is sealed in the wall of a blood vessel in a patient undergoing catheterization. Although the use of an introducer 10 adapted for catheterization is illustrated in FIG. 10, it is understood that the present invention is applicable to any type of procedure in which an introducer element is used to provide access to the lumen of a tubular tissue structure, such as a blood vessel, or to a body cavity. For example, the present invention is applicable to procedures in which an introducer element such as a needle, a cannula, a guide wire, an introducer element adapted for dialysis, a trocar, or any other introducer element used to access the lumen of a tubular tissue structure or to a body cavity is used.

As shown in the embodiment of the invention depicted in FIG. 10, an introducer 10 with a sheet 18 is inserted through the skin, the underlying muscle tissue, and through the blood vessel wall (FIG. 10A). As shown in FIG. 10A, the user proximal end 32 of the sheet 18 remains outside of the blood vessel wall and the user distal end 30 of the sheet 18 enters the blood vessel when the introducer 10 is inserted into the blood vessel. In the embodiment of the invention shown in FIG. 10, a positioning tube 44 is positioned between the sheath 16 and the sheet 18 and the positioning tube 44 is used to insert the sheet 18 to a predetermined position relative to the sheet 18 by causing resistance when the tapered ledge 42 of the positioning tube 44 reaches the outside of the vessel wall (see FIG. 10A including the enlarged view). The submucosal tissue or another extracellular matrix-derived tissue begins the remodeling process upon insertion of the introducer 10 and the sheet 18 through the blood vessel wall.

Figure 10B:
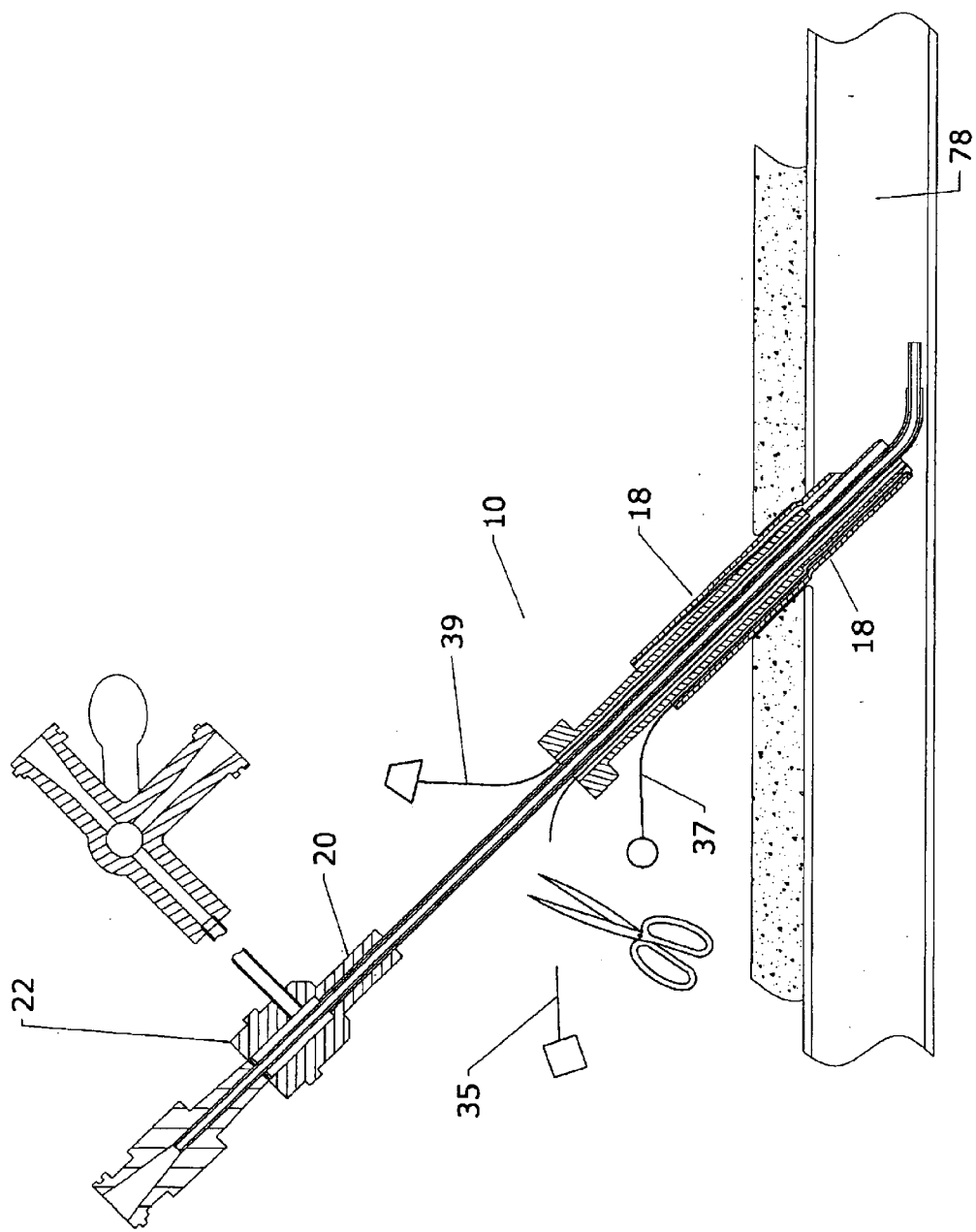
Figure 10D:
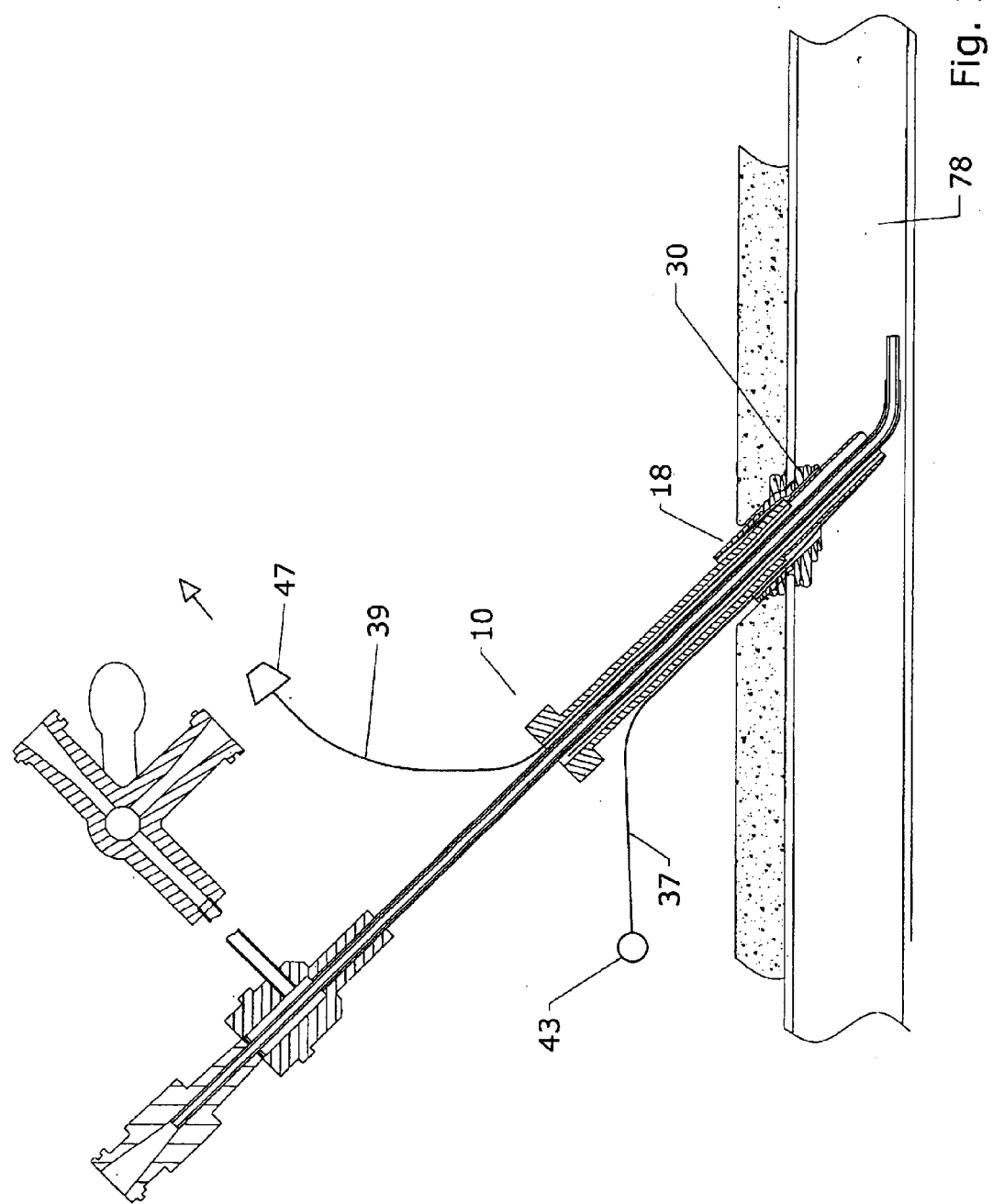
Figure 10F:
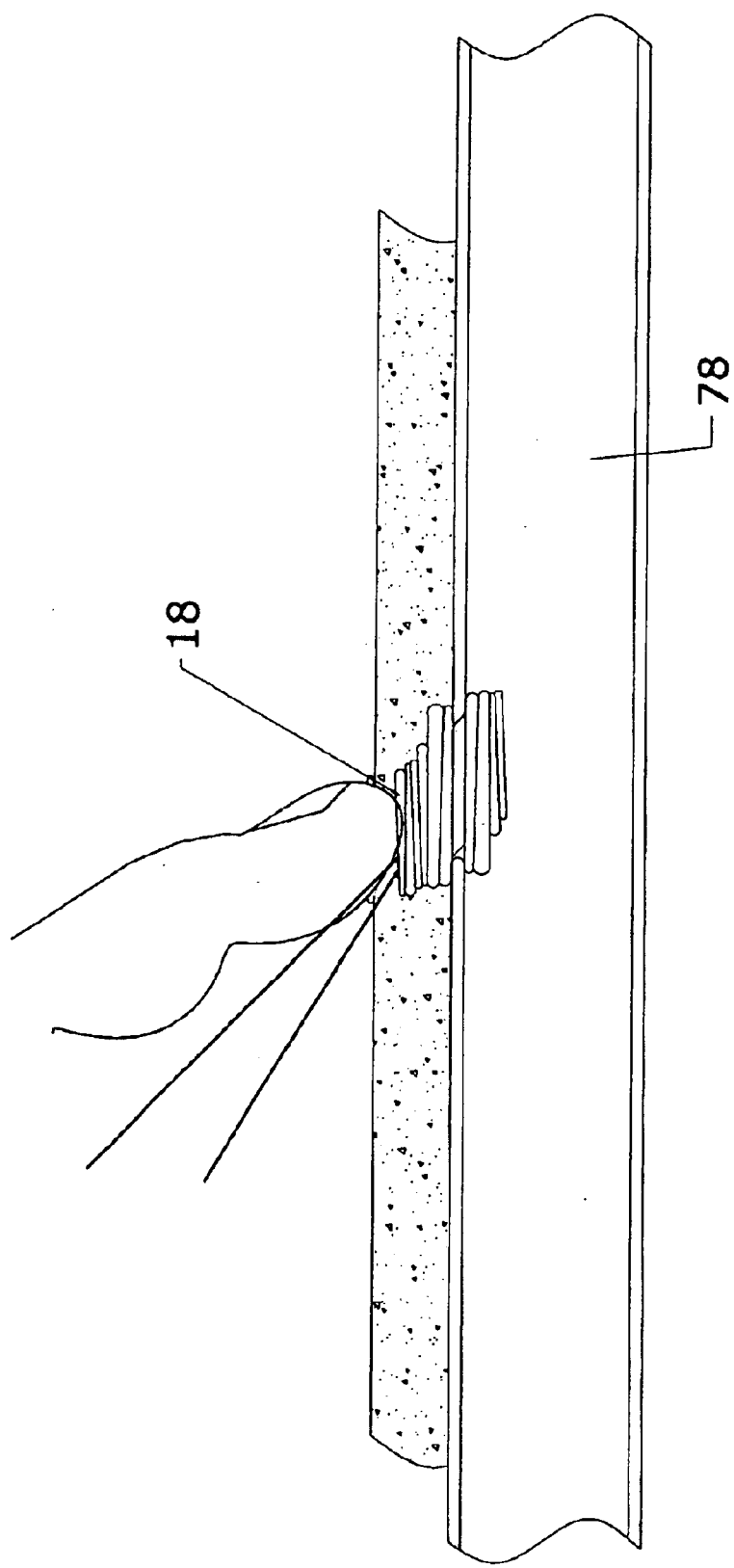
Figure 10G:
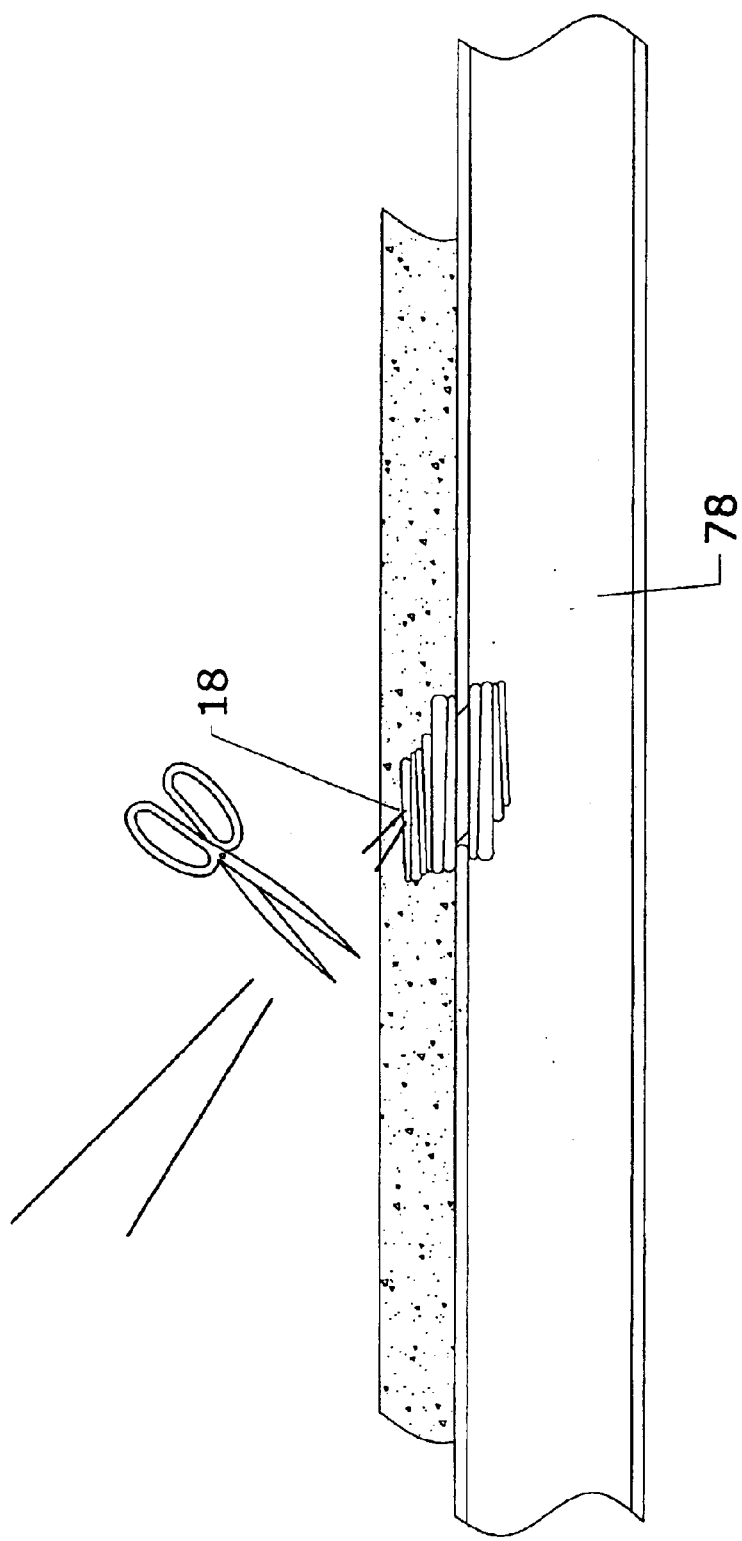

As is also shown in FIG. 10A, pull-up 37 and pull-down 39 tethers are attached at or near to the user distal end 30 and user proximal end 32 of the sheet 18, respectively, and are exposed externally. FIG. 10B depicts the cutting of the retaining tether 35 (e.g., a retaining tether 35 attached to the introducer 10, for example, to the sheath cap 20 or to the valve cap 22), so that the sheet 18 can be pulled up the introducer 10 using the pull-up tether 37. FIG. 10C shows how the puncture site is sealed by pulling the user proximal end 43 of the pull-up tether 37 to gather the sheet 18 in the puncture site in the blood vessel wall. The sheet 18 may be gathered along the guide wire as the guide wire is removed from the lumen of the blood vessel. As shown in FIG. 10D, the user proximal end 43 of the pull-up tether 37 is then pulled further to position the sheet 18 in the puncture site to form a hemostatic seal. As shown in FIGS. 10D–E, the unattached end 47 of the pull-down tether 39 is also pulled to gather the sheet 18 at the puncture site outside the vessel wall. As shown in FIG. 10E, as the introducer 10 is pulled out of the puncture site, the externally exposed end of the sheet 18 can be tucked under the skin, and can be further tucked under the skin as shown in FIG. 10F. As depicted in FIG. 10G, the sheet 18 forms a plug in the puncture site and remodels the connective tissue to form a hemostatic seal. The exposed portion of the tethers can be removed by cutting. In the above-described method, the sheet 18 can be gathered into the puncture site after, during, or before removal of any of the components of the introducer element.

What is claimed is:

1. A method of sealing a puncture site in the wall of a tubular tissue structure or in the wall of a body cavity, said method comprising the steps of:
    inserting an introducer element into the puncture site said introducer element having a sheet of submucosal tissue or another extracellular matrix-derived tissue of a warm-blooded vertebrate the sheet having a user distal end and a user proximal end;
    wherein the proximal end of the sheet remains outside of the punctured wall and the distal end of the sheet is positioned in the lumen of the tubular tissue structure or the body cavity; and
    wherein the sheet has at least one tether, and
    further comprising the step of tucking an end of the sheet under the skin after positioning the sheet within the puncture site.

2. A body structure intervention device having
    an extracorporeal portion,
    an intravascular portion,
    a lumen communicating between an intravascular space and an extracorporeal space,
    a tissue wall contact portion intermediate the extracorporeal and intravascular portions having an external surface for body tissue contact,
    a sheet of bioabsorbable material positioned in releasable contact with the tissue wall contact external surface and intravascular portions, and
    a tether.

3. A method of sealing a puncture site in the wall of a tubular tissue structure or in the wall of a body cavity, said method comprising the steps of:
    inserting an introducer element into the puncture site said introducer element having a releasably attached sheet comprising submucosal tissue or another extracellular matrix-derived tissue of a warm-blooded vertebrate such that a user distal end of the sheet is inserted into the tubular tissue structure or the body cavity and a user proximal end of the sheet remains outside of the punctured wall;
    providing the sheet with two or more tethers for positioning the distal end relative to the puncture site;
    pulling at least one tether to position the distal end of the sheet relative to the puncture site; and
    pulling the at least one tether to position the distal end of the sheet within the puncture site to seal the puncture site.

4. A method of sealing a puncture site in the wall of a tubular tissue structure or in the wall of a body cavity, said method comprising the steps of:
    inserting a guide wire into the tubular tissue structure or in the wall of the body cavity;
    inserting an introducer element into the puncture site said introducer element having a sheet comprising submucosal tissue or another extracellular matrix-derived tissue of a warm-blooded vertebrate the sheet having a user distal end and a user proximal end;
    wherein the proximal end of the sheet remains outside of the punctured wall while the distal end of the sheet is inserted into the tubular tissue structure or the body cavity; and
    wherein the sheet has at least one tether for positioning the distal end relative to the puncture site;
    pulling the tether to position the distal end of the sheet relative to the puncture site; and
    pulling the tether to position the distal end of the sheet within the puncture site to seal the puncture site.

5. A method of sealing a puncture site in the wall of a tubular tissue structure or in the wall of a body cavity, said method comprising the steps of:
    inserting a guide wire into the tubular tissue structure or in the wall of the body cavity;
    inserting an introducer element into the puncture site said introducer element having a sheet comprising submucosal tissue or another extracellular matrix-derived tissue of a warm-blooded vertebrate the sheet having a user distal end and a user proximal end;

wherein the proximal end of the sheet remains outside of the punctured wall while the distal end of the sheet is inserted into the tubular tissue structure or the body cavity; and wherein the sheet has at least one tether for positioning the distal end relative to the puncture site;

pulling the tether to position the distal end of the sheet relative to the puncture site; and pulling the tether to position the distal end of the sheet within the puncture site to seal the puncture site;

wherein the introducer element is removed from the tubular tissue structure or the wall of the body cavity prior to removing the guide wire and wherein the sheet is pulled along the guide wire.

6. A method of sealing a puncture site in the wall of a tubular tissue structure or in the wall of a body cavity, said method comprising the steps of:

inserting an introducer element adapted for dialysis into the puncture site said introducer element having a sheet comprising submucosal tissue or another extracellular matrix-derived tissue of a warm-blooded vertebrate the sheet having a user distal end and a user proximal end;

wherein the proximal end of the sheet remains outside of the punctured wall while the distal end of the sheet is inserted into the tubular tissue structure or the body cavity; and wherein the sheet has at least one tether for positioning the distal end relative to the puncture site;

pulling the tether to position the distal end of the sheet relative to the puncture site; and pulling the tether to position the distal end of the sheet within the puncture site to seal the puncture site.

7. A method of sealing a puncture site in the wall of a tubular tissue structure or in the wall of a body cavity, said method comprising the steps of:

inserting an introducer element into the puncture site said introducer element having a sheet comprising submucosal tissue or another extracellular matrix-derived tissue of a warm-blooded vertebrate the sheet having a user distal end and a user proximal end;

wherein the proximal end of the sheet remains outside of the punctured wall and the distal end of the sheet is inserted into the tubular tissue structure or the body cavity; and wherein the sheet has at least one tether for positioning the distal end relative to the puncture site;

pulling the tether to position the distal end of the sheet relative to the puncture site;

pulling the tether to position the distal end of the sheet within the puncture site to seal the puncture site; and tucking an externally exposed end of the sheet under the skin after positioning the sheet within the puncture site.

8. A method of sealing a puncture site in the wall of a tubular tissue structure or in the wall of a body cavity, said method comprising the steps of:

inserting an introducer element into the puncture site said introducer element having a sheet comprising submucosal tissue or another extracellular matrix-derived tissue of a warm-blooded vertebrate the sheet having a user distal end and a user proximal end;

wherein the sheet is inserted into the tubular tissue structure or the body cavity to a predetermined position relative to the sheet by using a positioning tube having a tapered ledge adapted to indicate when the predetermined position is reached;

wherein the proximal end of the sheet remains outside of the punctured wall while the distal end of the sheet is inserted into the tubular tissue structure or the body cavity; and wherein the sheet has at least one tether for positioning the distal end relative to the puncture site;

pulling the tether to position the distal end of the sheet relative to the puncture site; and pulling the tether to position the distal end of the sheet within the puncture site to seal the puncture site.

9. An apparatus for sealing a puncture site in the wall of a tubular tissue structure or the wall of a body cavity in a patient said apparatus comprising:

an introducer element; and a sheet of submucosal tissue or another extracellular matrix-derived tissue said sheet having a user distal end and a user proximal end;

wherein the introducer element further comprises a positioning tube having a tapered ledge and located between the sheet and the introducer element for inserting the sheet into the tubular tissue structure or the body cavity to a predetermined position relative to the sheet, the tapered ledge being adapted to indicate when the predetermined position is reached.

10. A method of sealing a puncture site comprising inserting an elongated element with a bioabsorbable member releasably attached to at least an exterior portion of the elongated element into the puncture site so that the bioabsorbable material contacts the puncture site tissue, and removing the elongated element so that the bioabsorbable material extends both inside and outside the puncture site and seals the puncture site.

* * * * *